United States Patent
Higashimura et al.

(10) Patent No.: US 8,048,982 B2
(45) Date of Patent: Nov. 1, 2011

(54) METHOD FOR PRODUCING AROMATIC COMPOUND POLYMER

(75) Inventors: Hideyuki Higashimura, Tsukuba (JP); Daisuke Fukushima, Tsukuba (JP); Kazuei Ohuchi, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 740 days.

(21) Appl. No.: 11/571,280

(22) PCT Filed: Jun. 24, 2005

(86) PCT No.: PCT/JP2005/012165
§ 371 (c)(1),
(2), (4) Date: May 20, 2008

(87) PCT Pub. No.: WO2006/001519
PCT Pub. Date: Jan. 5, 2006

(65) Prior Publication Data
US 2009/0018309 A1    Jan. 15, 2009

(30) Foreign Application Priority Data
Jun. 28, 2004    (JP) ................................ 2004-189397

(51) Int. Cl.
*C08G 65/00* (2006.01)
*C08G 65/34* (2006.01)
*C07F 9/00* (2006.01)

(52) U.S. Cl. ............................ 528/425; 528/480; 556/42

(58) Field of Classification Search .................. 528/425, 528/480; 556/42
See application file for complete search history.

(56) References Cited

U.S. PATENT DOCUMENTS
4,902,776 A    2/1990    Hirai et al.

FOREIGN PATENT DOCUMENTS

| EP | 0352882 A1 | 1/1990 |
|----|----|----|
| JP | 63-202626 A | 8/1988 |
| JP | 10-174879 A | 6/1998 |
| JP | 10-292034 A | 11/1998 |
| JP | 10-292035 A | 11/1998 |

OTHER PUBLICATIONS

Multi-Electron Transfer Process of Vanadyl Complexes for Oxidative Polymerization of Diphenyl Disulfide; Yamamoto et al.; Polymers for Advanced Technologies; Mar. 1, 1995, No. 3, vol. 6; pp. 155-158.
Synthesis and Characterization of Regiocontrolled Poly (2, 5-di-n-butoxy-1, 4-phenylene) by Oxovanadium-Catalyzed Oxidative Coupling Polymerization; Okada et al.; Macromolecules; Nov. 18, 1996, vol. 29, No. 24; pp. 7645-7650.
Oxidative Polymerization of Pyrrole with a Vanadium Dinulcear Complex as a Two-Electron Redox Catalyst; Tshuchida et al.; Journal of the Electroanalytical Chemistry; Mar. 17, 1996, vol. 438, No. 1; pp. 167-171.
Synthesis of Polyethers by Oxovanadium-Catalyzed Oxidative Coupling Polymerization of di (1-naphthoxy) Compounds; Okada et al.; Reactive & Functional Polymers; Jun. 1, 1996, vol. 30, No. 1; pp. 157-163.

*Primary Examiner* — Duc Truong
(74) *Attorney, Agent, or Firm* — Sughrue Mion, PLLC

(57) ABSTRACT

A method for producing an aromatic compound polymer comprising oxidatively polymerizing one or more of aromatic compound(s) having two or more hydrogen atoms directly connected to aromatic ring(s), in the presence of an oxidizing agent, wherein the method employs a catalyst composed of a transition metal complex or a catalyst prepared from a transition metal complex and an activating agent, and said catalyst has a parameter P defined by the following formula (A) of 0.50 or more, and a parameter Eo defined by the following formula (B) of 0.50 [V] or more:

$$P = Af/Ai \qquad (A)$$

and $$Eo = (Epa + Epc)/2 \ [V] \qquad (B).$$

11 Claims, No Drawings

METHOD FOR PRODUCING AROMATIC COMPOUND POLYMER

TECHNICAL FIELD

The present invention relates to a method for producing an aromatic compound polymer.

BACKGROUND ART

Aromatic compound polymers such as polyarylene and the like are useful as functional materials such as fluorescent polymer materials, conductive polymer materials and the like, and as the methods for producing thereof, methods of oxidatively polymerizing an aromatic compound in the presence of a vanadium complex catalytic system and an oxidizing agent are known (Literatures 1 and 2).

[Literature 1] Journal of Electroanalytical Chemistry 1997, 438, 167

[Literature 2] Macromolecules 1996, 29, 7645

For example, Literature 1 discloses a method of polymerizing pyrrole by using a catalyst prepared from (N,N'-ethylenebis(salycylideneaminato))oxovanadium(IV) (VO(salen)) and an acid, as the catalyst, in the presence of oxygen.

The catalytic system used in the method of Literature 1, however, hardly promotes a polymerization reaction when being applied to polymerization of p-dialkoxybenzene.

Literature 2 discloses a method for producing a polymer wherein p-dialkoxybenzene is polymerized in the presence of oxygen, by using a catalyst prepared from vanadyl acetylacetonato (VO(acac)$_2$) and an acid under co-presence of anhydrous trifluoroacetic acid as a dehydrating agent of which amount is 2 equivalent per p-dialkoxybenzene as the raw material.

This method has a problem that polymerization seldom proceeds without co-presence of a large amount of a dehydrating agent.

As mentioned above, the conventional methods occasionally result in very low yield of polymer depending on the kind of an aromatic compound as the raw material, and a large amount of a dehydrating agent is required to polymerize such raw material, accordingly, this case is not always preferable for industrial production because of purification of the intended polymer becomes difficult.

DISCLOSURE OF THE INVENTION

The object of the present invention is to provide, for oxidatively polymerizing an aromatic compound, a method for producing an aromatic compound polymer wherein the polymer can be obtained in a relatively good yield without using a large amount of a dehydrating agent.

The inventors have intensively studied to solve the above problems, and have found a fact that oxidatively polymerizing an aromatic compound by using a specific catalyst allows to produce corresponding aromatic compound polymer in a relatively good yield without using large amount of a dehydrating agent, and then achieved the invention.

That is, the invention provides a method for producing an aromatic compound polymer by oxidatively polymerizing one or more of aromatic compound(s) having two or more hydrogen atoms directly connected to aromatic ring(s), in the presence of an oxidizing agent, wherein the method employs a catalyst being composed of a transition metal complex or a catalyst prepared from a transition metal complex and an activating agent, and said catalyst has a parameter P defined by the following formula (A) of 0.50 or more, and a parameter Eo defined by the following formula (B) of 0.50 [V] or more:

$$P = Af/Ai \tag{A}$$

wherein Ai represents an absorbance at an absorption maximum belonging in an absorption band located at the longest wavelength side in an absorption spectrum obtained for a solution containing the catalyst, in a ultraviolet to near-infrared wavelength region from 200 nm to 800 nm, and Af represents an absorbance at the same wavelength applied to the Ai, in an absorption spectrum in the above wavelength region obtained for a solution prepared by adding 3 equivalent of water per mole of the metal contained in the catalyst to the solution.

$$Eo = (Epa + Epc)/2 [V] \tag{B}$$

wherein, Epa represents a peak potential at the oxidation side of an oxidation-reduction potential derived from the transition metal contained in the catalyst, at a potential of 0.50 [V] or more based on oxidation-reduction potential of ferrocene/ferrocenium ion measured with a cyclic voltammetry for the solution containing the catalyst, and Epc represents a peak potential at the reduction side corresponding to Epa by the same measurement.

BEST MODE FOR CARRYING OUT THE INVENTION

The aromatic compound used as a raw material for the production method of the invention is the one having two or more hydrogen atoms directly connected to aromatic ring(s). The aromatic compound, for example, is exemplified by a structure represented by the following general formula (2):

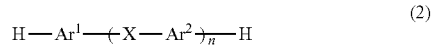

wherein $Ar^1$ and $Ar^2$ each independently represent arylene group or divalent aromatic heterocyclic group; X represents a single bond or divalent bonding structure; and n represents an integer of zero or more; and when X and $Ar^2$ exist in a plural number respectively, they may respectively be same or different from each other.

The n in the above formula (2) represents an integer of zero or more. For the aromatic compound used as a raw material for the production method of the invention, in view of the reactivity thereof, n in the formula (2) is preferably 100 or less, more preferably 10 or less, even more preferably 0 or 1, and particularly preferably 0.

The divalent bonding structure is exemplified by those represented by the following formulas (L-1) to (L-25) and a combination of 2 or more thereof:

-continued

L-4 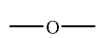
L-5 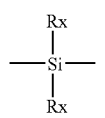
L-6 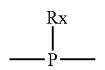
L-7 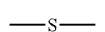
L-8 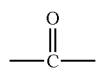
L-9 
L-10 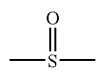
L-11 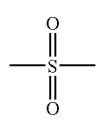
L-12 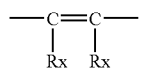
L-13 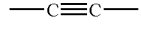
L-14 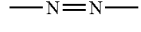
L-15 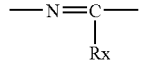
L-16 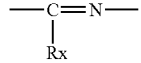
L-17 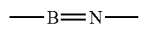
L-18 
L-19 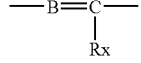
L-20 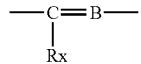
L-21 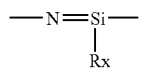
L-22 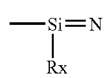
L-23 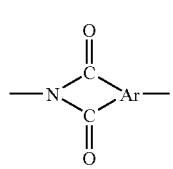
L-24 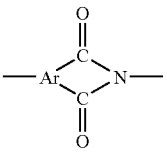
L-25 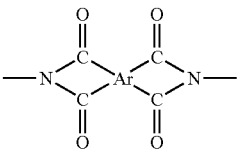

wherein Rxs each independently represent a hydrogen atom or a group selected from the group consisting of alkyl group, aryl group, aralkyl group, and monovalent heterocyclic group; such groups may further have a substituent on a carbon atom thereof; when Rx exist in a plural number, it may combine each other to form a ring; and Ar represents a divalent to tetravalent aromatic hydrocarbon having about 6 to 60 carbon atoms or a divalent to tetravalent aromatic heterocyclic compound having about 2 to 60 carbon atoms.

Those combined with 2 or more of above-described formulas are exemplified by the following formulas (LL-1) to (LL-10):

LL-1 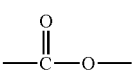
LL-2 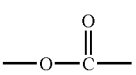
LL-3 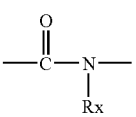
LL-4 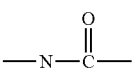
LL-5 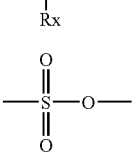
LL-6 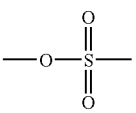
LL-7 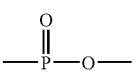
LL-8 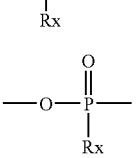

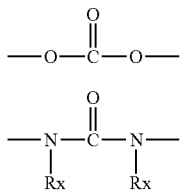

LL-9

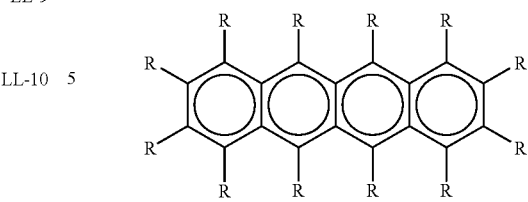

LL-10

(wherein Rx represents the same meaning described above).

X is preferably a single bond or divalent bonding structures represented by the formulas (L-2 to L-5, L-8 to L-13, L-15, L-16, L-23 to L-25, and LL-1 to LL-10), more preferably a single bond or divalent bonding structures represented by the formulas (L-2 to L-4, L-8, L-11, L-12, and L-23 to L-25), even more preferably a single bond or divalent bonding structures represented by the formulas (L-2 to L-4 and L-12), and particularly preferably a single bond or divalent bonding structures represented by the formulas (L-2 to L-4).

The arylene group is an atomic group excluding 2 hydrogen atoms from an aromatic hydrocarbon, also including the one having a condensed ring. The arylene group may have a substituent. The number of carbon atoms contained in the portion left after removing a substituent from the arylene group is usually about 6 to 60, and preferably 6 to 20. The total number of carbon atoms contained in the arylene group including a substituent thereof is usually about 6 to 100. The arylene group is exemplified by the following formulas 1A-1 to 1A-10 and 1B-1 to 1B-7:

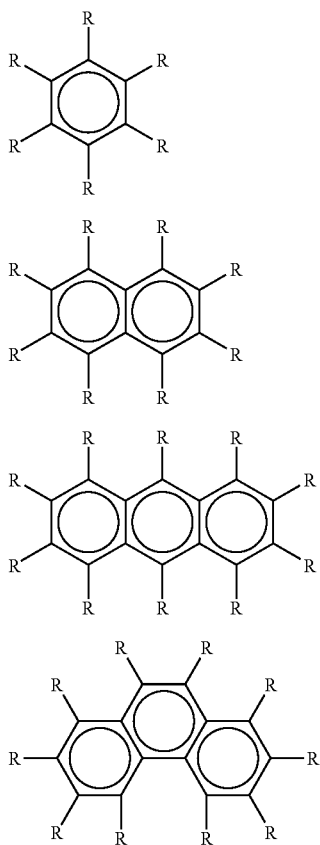

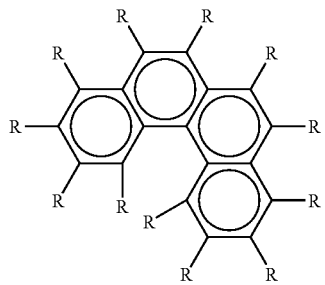

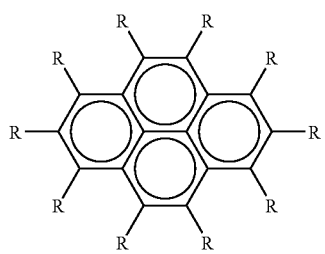

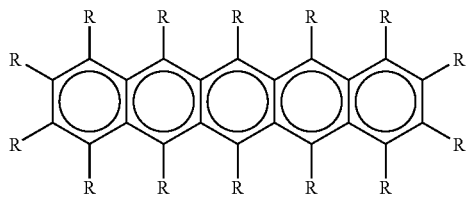

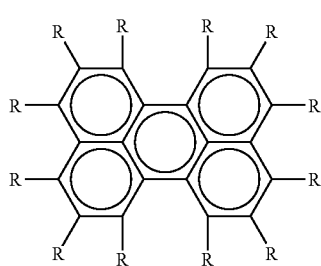

-continued

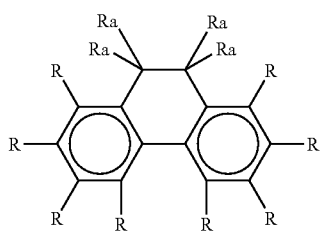

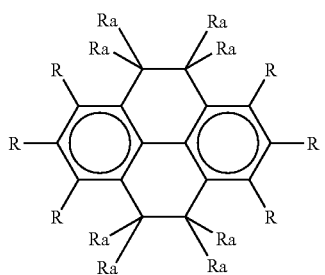

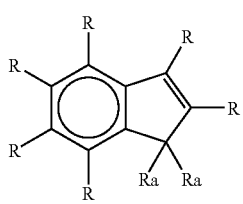

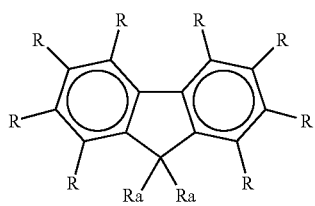

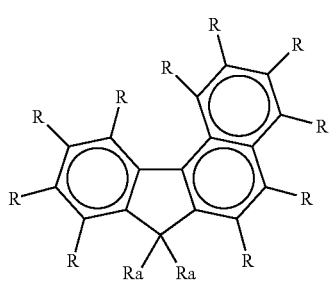

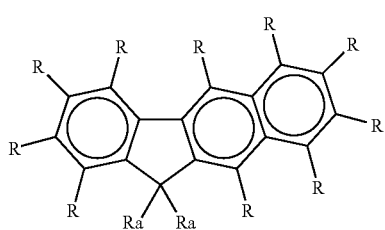

-continued 1B-1

1B-2

1B-3

1B-4

1B-5

1B-6

1B-7

In the above formulas 1A-1 to 1A-10 and 1B-1 to 1B-7, Rs each independently represent a hydrogen atom; alkyl group, aryl group, aralkyl group, and monovalent heterocyclic group; optionally substituted formyl groups such as formyl group, substituted carbonyl group, carboxylic acid group, and substituted oxycarbonyl group; optionally substituted thioformyl groups such as thioformyl group and substituted thiocarbonyl group, and optionally substituted imine residue; optionally substituted hydroxy groups such as hydroxy group, alkoxy group, aryloxy group, aralkyloxy group, and substituted carbonyloxy group; optionally substituted mercapto groups such as mercapto group, alkylthio group, arylthio group, aralkylthio group, and substituted carbonylthio group; optionally substituted amino groups such as amino group, substituted amino group, amide group, and acidimide group, halogen atom, substituted sulfonyl group, optionally substituted silyl group, optionally substituted silanol group, sulfonic acid group, phosphono group, cyano group, nitro group, disulfide residue, and disubstituted phosphino group; or a bonding with a hydrogen atom or a bonding structure represented by X in the general formula (2) (hereinafter, sometimes referred to as a connecting bond). Two of Rs represent the connecting bonds. Ra each independently represent a hydrogen atom, alkyl group, aryl group, aralkyl group, and monovalent heterocyclic group; optionally substituted formyl groups such as formyl group, substituted carbonyl group, carboxylic acid group, and substituted oxycarbonyl group; optionally substituted thioformyl groups such as thioformyl group and substituted thiocarbonyl group, and optionally substituted imine residue; optionally substituted hydroxy groups such as hydroxy group, alkoxy group, aryloxy group, aralkyloxy group, and substituted carbonyloxy group; optionally substituted mercapto groups such as mercapto group, alkylthio group, arylthio group, aralkylthio group, and substituted carbonylthio group; optionally substituted amino groups such as amino group, substituted amino group, amide group, and acidimide group, and halogen atom. When two Ras exist on the same atom, those two may combine to form oxo group, thioxo group, and seleno group, or form a ring by bonding each other.

Among the groups represented by R described above, the groups located on the atoms being adjacent on an aromatic ring may combine each other to form a condensed ring, the condensed ring being 5 to 7 membered aliphatic ring optionally containing a hetero atom such as an oxygen atom, sulfur atom, nitrogen atom and the like, or an aromatic hydrocarbon ring.

Arylene groups represented by $Ar^1$ and $Ar^2$ are preferably phenylene group (Formula 1A-1), naphthalene-diyl group (1A-2), anthracene-diyl group (1A-3), fluorene-diyl group (1B-4), and indenonaphthalene-diyl group (1B-5 to 1B-7).

The divalent aromatic heterocyclic group is an atomic group excluding 2 hydrogen atoms from an aromatic heterocyclic compound, also including the one having a condensed ring. The aromatic heterocyclic compound, in organic compounds having a ring structure, means the one having not only a carbon atom but also a hetero atom such as oxygen, sulfur, nitrogen, phosphorus, boron, silicon, and selenium in the ring thereof as atoms structuring the ring. The divalent aromatic heterocyclic group may have a substituent. The number of carbon atoms contained in the portion left after removing a substituent from the divalent aromatic heterocyclic group is usually about 2 to 60, and preferably 2 to 20. The total number of carbon atoms contained in the divalent aromatic heterocyclic group including a substituent thereof is usually about 2 to 100. The divalent aromatic heterocyclic group is exemplified by the following formulas 2A-1 to 2A-17, 2B-1 to 2B-14, 2C-1 to 2C-12, 2D-1 to 2D-7, 2E-1 to 2E-6, and 2F-1 to 2F-2:

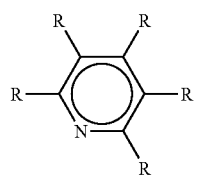
2A-1

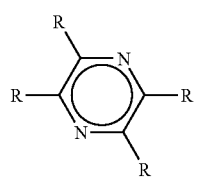
2A-2

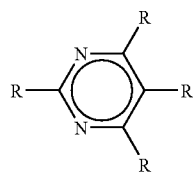
2A-3

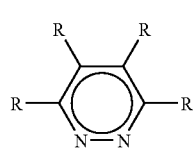
2A-4

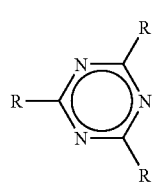
2A-5

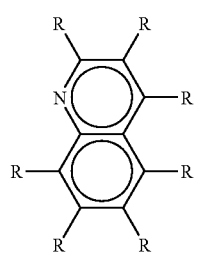
2A-6

-continued

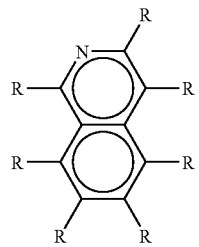
2A-7

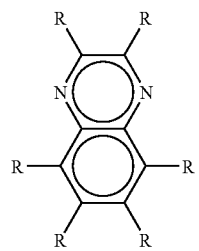
2A-8

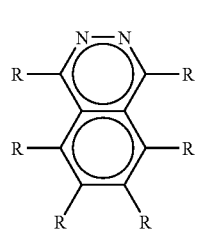
2A-9

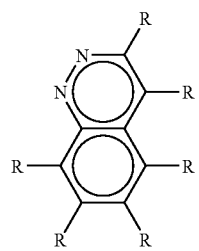
2A-10

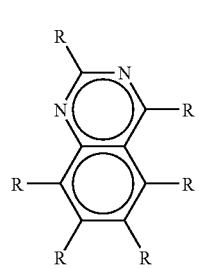
2A-11

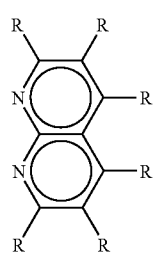
2A-12

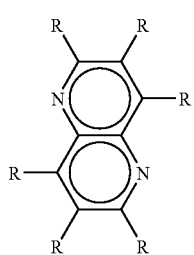
2A-13
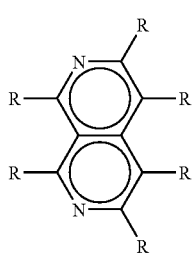
2A-14
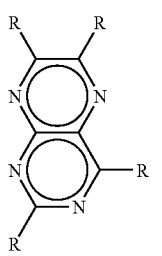
2A-15
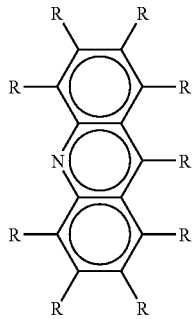
2A-16
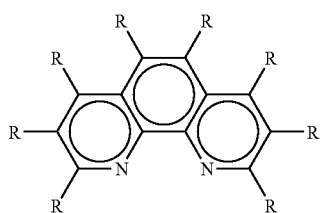
2A-17
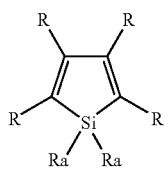
2B-1
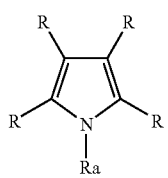
2B-2
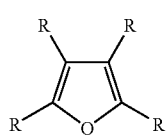
2B-3
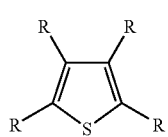
2B-4
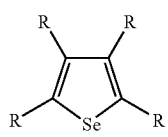
2B-5
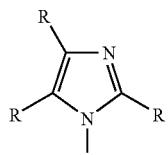
2B-6
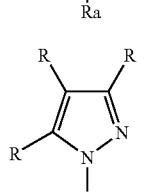
2B-7
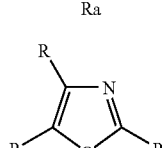
2B-8
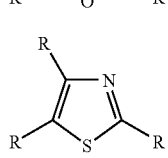
2B-9
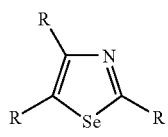
2B-10
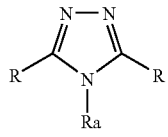
2B-11
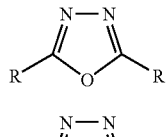
2B-12
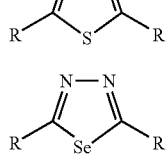
2B-13
2B-14

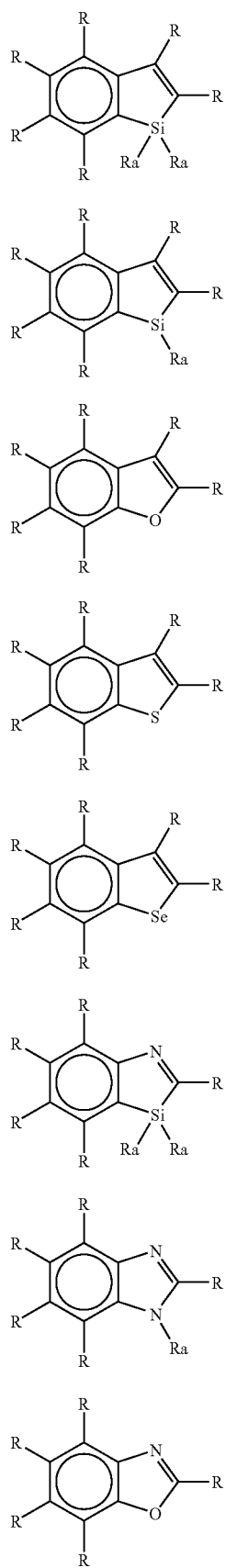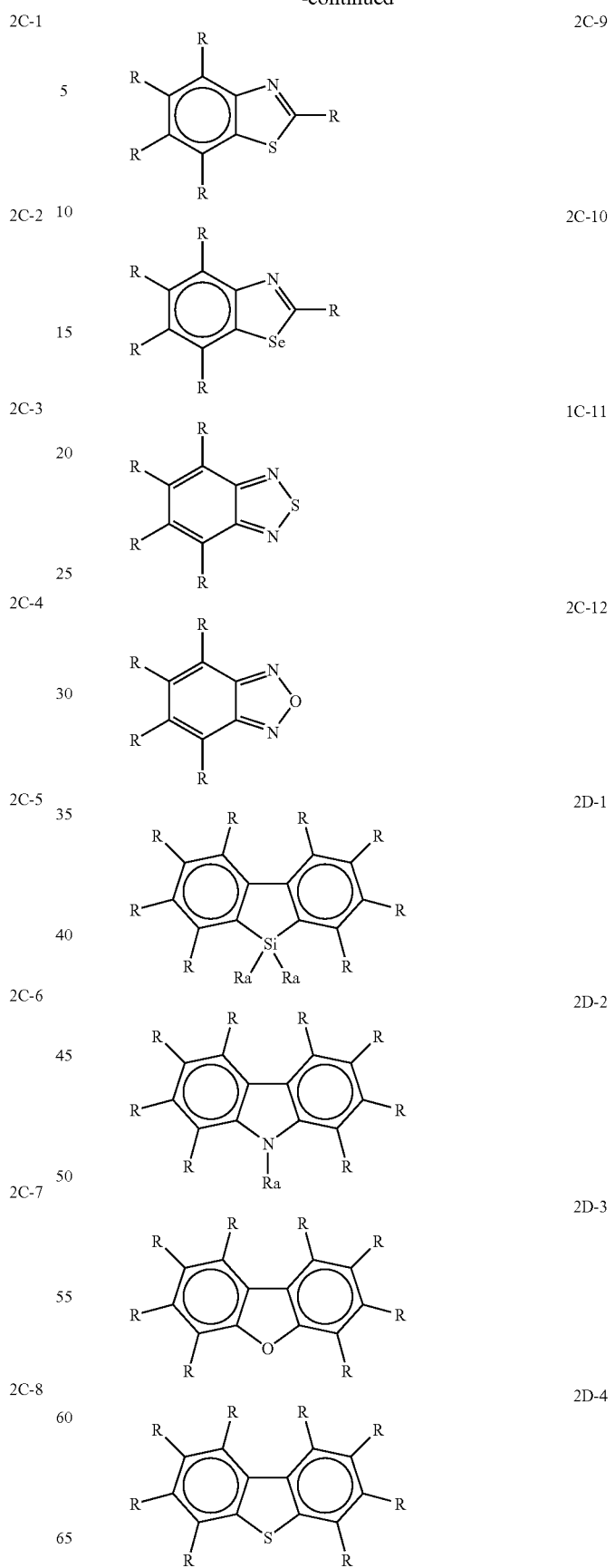

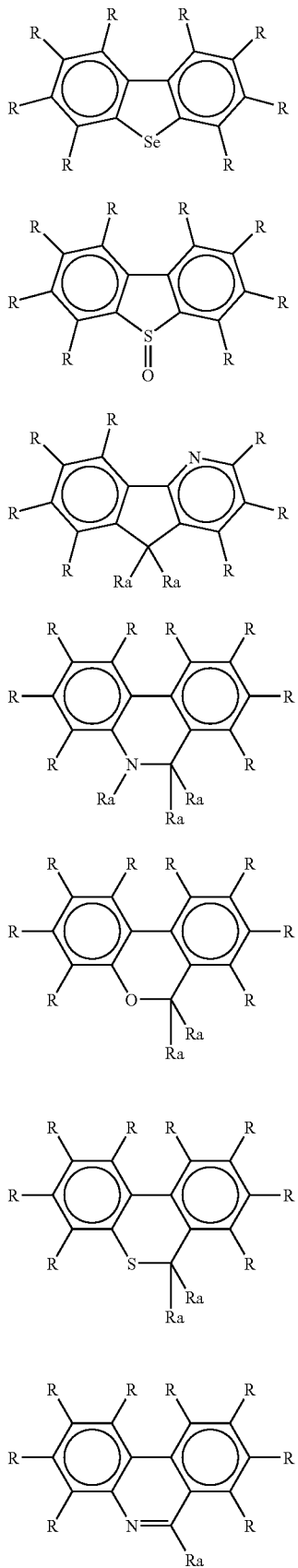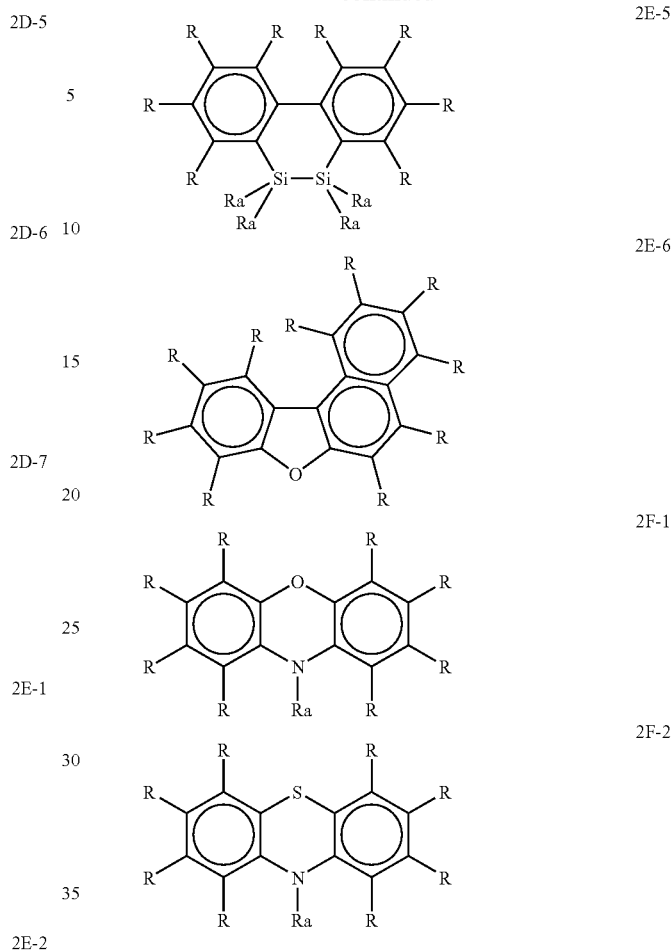

In the above described formulas 2A-1 to 2A-17, 2B-1 to 2B-14, 2C-1 to 2C-12, 2D-1 to 2D-7, 2E-1 to 2E-6, and 2F-1 to 2F-2, R and Ra represent the same meanings mentioned above.

Among the groups represented by R mentioned above, the groups located on the atoms being adjacent on an aromatic ring may combine each other to form a condensed ring, the condensed ring being 5 to 7 membered aliphatic ring optionally containing a hetero atom such as an oxygen atom, sulfur atom, nitrogen atom and the like, aromatic heterocyclic ring or an aromatic hydrocarbon ring.

Divalent aromatic heterocyclic groups represented by $Ar^1$ and $Ar^2$ are preferably 5 membered heterocyclic group (Formula 2C-1 to 2C-12) having a condensed benzene ring containing a hetero atom such as a silicon atom, nitrogen atom, oxygen atom, and sulfur atom; heterocyclic group having a fluorene-like structure (2D-1 to 2D-7) containing a hetero atom such as a silicon atom, nitrogen atom, oxygen atom, and sulfur atom; and heterocyclic group having a condensed ring structure represented by the formulas (2E-1 to 2E-6 and 2F-1 to 2F-2).

R includes preferably a hydrogen atom, alkyl group, aryl group, aralkyl group, monovalent heterocyclic group, alkoxy group, aryloxy group, aralkyloxy group, alkylthio group, arylthio group, aralkylthio group, and substituted amino group, and more preferably a hydrogen atom, alkyl group, alkoxy group, and aralkylthio group.

Ra includes preferably a hydrogen atom, alkyl group, aryl group, aralkyl group, monovalent heterocyclic group, formyl group, substituted carbonyl group, carboxylic acid group, substituted oxycarbonyl group, hydroxy group, alkoxy group, aryloxy group, aralkyloxy group, alkylthio group, arylthio group, and aralkylthio group, more preferably a hydrogen atom, alkyl group, aryl group, aralkyl group, and monovalent heterocyclic group, and even more preferably alkyl group.

Rx includes preferably a hydrogen atom, alkyl group, aryl group, and aralkyl group, and more preferably a hydrogen atom and alkyl group.

The groups represented by R, Ra or Rx are exemplified with alkyl group, aryl group, aralkyl group, and monovalent heterocyclic group (which are represented by the formula R-1); optionally substituted formyl groups (the formulas R-2 to R-5) such as formyl group and substituted carbonyl group (which are represented by the formula R-2), and carboxylic acid group and substituted oxycarbonyl group (which are represented by the formula R-3); optionally substituted thioformyl groups (the formulas R-6 to R-9) such as thioformyl group and substituted thiocarbonyl group (which are represented by the formula R-6); optionally substituted imine residue (the formulas R-10 to R-13, and R-26); optionally substituted hydroxy groups (the formulas R-14 to R-17) such as hydroxy group, alkoxy group, aryloxy group, and aralkyloxy group (which are represented by the formula R-14), and substituted carbonyloxy group (the formula R-15); optionally substituted mercapto groups (the formulas R-18 to R-21) such as mercapto group, alkylthio group, arylthio group, and aralkylthio group (which are represented by the formula R-18), and substituted carbonylthio group (the formula R-19); optionally substituted amino groups (the formulas R-22 to R-25, and R-27) such as amino group and substituted amino group (which are represented by the formula R-22), amide group (the formula R-23), and acidimide group (the formula R-27); halogen atom (the formulas R-28 to R-31); substituted sulfonyl group (the formula R-32); optionally substituted silyl group (the formula R-33); optionally substituted silanol group (the formula R-34); sulfonic acid group (the formula R-35); phosphono group (the formula R-36); cyano group (the formula R-37); nitro group (the formula R-38); disulfide residue (the formula R-39); and disubstituted phosphino group (the formula R-40):

—R'

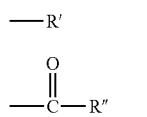  R-1

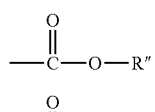  R-2

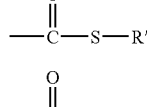  R-3

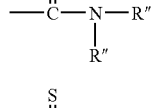  R-4

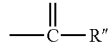  R-5

R-6

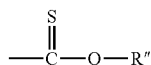  R-7

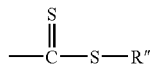  R-8

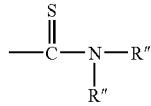  R-9

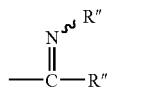  R-10

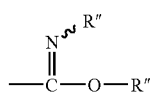  R-11

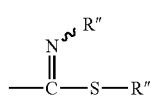  R-12

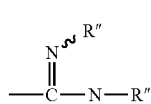  R-13

  R-14

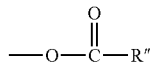  R-15

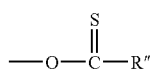  R-16

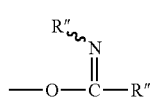  R-17

  R-18

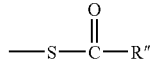  R-19

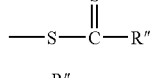  R-20

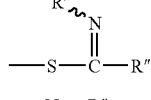  R-21

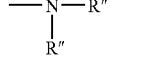  R-22

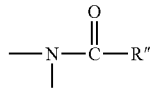  R-23

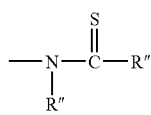  R-24

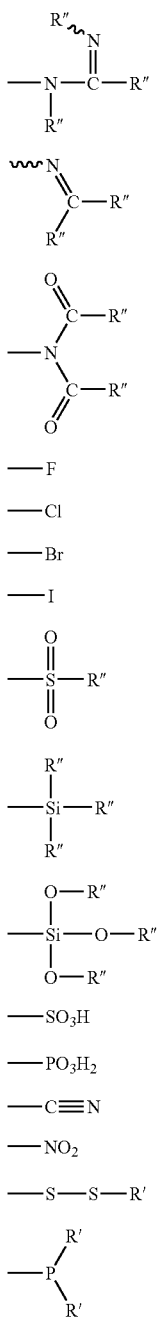

wherein R' represents a group selected from the group consisting of alkyl group, aryl group, aralkyl group, and monovalent heterocyclic group; and R" represents a hydrogen atom or a group selected from the group consisting of alkyl group, aryl group, aralkyl group, and monovalent heterocyclic group;

The alkyl group represented by R' and R" may be either linear, branched or cyclic, usually having about 1 to 50 carbon atoms; the specific examples thereof include methyl group, ethyl group, propyl group, isopropyl group, n-butyl group, isobutyl group, s-butyl group, t-butyl group, pentyl group, iso pentyl group, hexyl group, cyclohexyl group, heptyl group, norbornyl group, octyl group, 2-ethylhexyl group, nonyl group, decyl group, 3,7-dimethyloctyl group, adamantyl group, dodecyl group, cyclododecyl group, and octadecyl group. In view of solubility to organic solvents and easiness of synthesis, the alkyl group is preferably the one having 1 to 20 carbon atoms, and more preferably having 1 to 16 carbon atoms.

The aryl group represented by R' and R" is an atomic group excluding 1 hydrogen atom on the aromatic ring from an aromatic hydrocarbon, and also including the one having a condensed ring. The aryl group has usually about 6 to about 60 carbon atoms, and preferably 7 to 48; being specifically exemplified with an aryl group being adding one hydrogen atom to the arylene group represented by $Ar^1$ and $Ar^2$ mentioned above, more specifically phenyl group, $C_1$ to $C_{12}$ alkylphenyl group (hereinafter, $C_1$ to $C_{12}$ being referred to as 1 to 12 carbon numbers), 1-naphthyl group, 2-naphthyl group, 1-anthracenyl group, 2-anthracenyl group, and 9-anthracenyl group.

The $C_1$ to $C_{12}$ alkylphenyl group is specifically exemplified with methylphenyl group, ethylphenyl group, dimethylphenyl group, dimethyl-t-butylphenyl group, propylphenyl group, mesityl group, methylethylphenyl group, isopropylphenyl group, n-butylphenyl group, isobutylphenyl group, s-butylphenyl group, t-butylphenyl group, pentylphenyl group, isopentylphenyl group, hexylphenyl group, heptylphenyl group, octylphenyl group, nonylphenyl group, decylphenol group, 3,7-dimethyloctylphenyl group, and dodecylphenyl group.

In view of solubility to organic solvents and easiness of synthesis, the aryl group is preferably phenyl group and $C_1$ to $C_{12}$ alkylphenyl group.

The aralkyl group represented by R' and R" has usually about 7 to about 60 carbon atoms, and preferably 7 to 48; being specifically exemplified with phenyl-$C_1$ to $C_{12}$ alkyl group, $C_1$ to $C_{12}$ alkylphenyl-$C_1$ to $C_{12}$ alkyl group, 1-naphthyl-$C_1$ to $C_{12}$ alkyl group, and 2-naphthyl-$C_1$ to $C_{12}$ alkyl group.

In view of solubility to organic solvents and easiness of synthesis, phenyl-$C_1$ to $C_{12}$ alkyl group and $C_1$ to $C_{12}$ alkylphenyl-$C_1$ to $C_{12}$ alkyl group are preferable.

The monovalent heterocyclic group represented by R' and R" is an atomic group excluding 1 hydrogen atom from an heterocyclic compound, and the carbon numbers thereof is usually about 4 to about 60, and preferably 4 to 20. However, the carbon numbers of the heterocyclic group do not contain the carbon numbers of the substituted group thereof. The heterocyclic compound, in organic compounds having a ring structure, means the one having not only a carbon atom but also a hetero atom such as oxygen, sulfur, nitrogen, phosphorus, and boron in the ring thereof as atoms structuring the ring; being specifically exemplified with monovalent aromatic heterocyclic group being adding one hydrogen atom to the divalent aromatic heterocyclic group represented by $Ar^1$ and $Ar^2$ mentioned above, and aliphatic heterocyclic group such as pyrrolidyl group, piperidyl group, piperazyl group, morpholyl group, tetrahydrofuranyl group, tetrahydrothiophenyl group, tetrahydropyranyl group, and dihydropyranyl group.

When the group represented by R' and R" is alkyl group, aryl group, aralkyl group, or monovalent heterocyclic group, a hydrogen atom on the alkyl group, aryl group, aralkyl group, or monovalent heterocyclic group may be further substituted with a group represented by the above-mentioned formulas (R-1 to R-40). The substituent further substituting the alkyl group, aryl group, aralkyl group, or monovalent heterocyclic group is preferably formyl group optionally substituted with alkyl group, thiof ormyl group optionally substituted with alkyl group, imine residue optionally substituted with alkyl group, hydroxy group optionally substituted with alkyl group, mercapto group optionally substituted with alkyl group, amino group optionally substituted with alkyl group, halogen atom, sulfonyl group substituted with alkyl group, silyl group optionally substituted with alkyl group, silanol group optionally substituted with alkyl group, sulfonic acid group, phosphono group, cyano group, nitro group, aryldisulfide group, and diarylphosphino group, more preferably alkoxy group, alkylthio group, and dialkylamino group, and even more preferably alkoxy group and alkylthio group. The group represented by R' and R'' further having substituent as mentioned above are specifically exemplified, for example, with groups having $C_1$ to $C_{12}$ alkoxy substitution such as $C_1$ to $C_{12}$ alkoxyphenyl group, $C_1$ to $C_{12}$ alkoxyphenyl-$C_1$ to $C_{12}$ alkyl group, $C_1$ to $C_{12}$ alkoxyphenylaminocarbonyl group, di($C_1$ to $C_{12}$ alkoxyphenyl)aminocarbonyl group, $C_1$ to $C_{12}$ alkoxyphenyl-$C_1$ to $C_{12}$ alkylaminocarbonyl group, di($C_1$ to $C_{12}$ alkoxyphenyl-$C_1$ to $C_{12}$ alkyl)aminocarbonyl group, $C_1$ to $C_{12}$ alkoxyphenoxy group, $C_1$ to $C_{12}$ alkoxyphenyl-$C_1$ to $C_{12}$ alkoxy group, $C_1$ to $C_{12}$ alkoxyphenylthio group, $C_1$ to $C_{12}$ alkoxyphenyl-$C_1$ to $C_{12}$ alkylthio group, $C_1$ to $C_{12}$ alkoxyphenylamino group, di($C_1$ to $C_{12}$ alkoxyphenyl)amino group, $C_1$ to $C_{12}$ alkoxyphenyl-$C_1$ to $C_{12}$ alkylamino group, di($C_1$ to $C_{12}$ alkoxyphenyl-$C_1$ to $C_{12}$ alkyl)amino group, and $C_1$ to $C_{12}$ alkoxyphenyl-$C_1$ to $C_{12}$ alkylsilyl group. The $C_1$ to $C_{12}$ alkoxy is specifically exemplified with methoxy, ethoxy, propyloxy, isopropyloxy, n-butoxy, isobutoxy, s-butoxy, t-butoxy, pentyloxy, hexyloxy, cyclohexyloxy, heptyloxy, octyloxy, 2-ethylhexyloxy, nonyloxy, decyloxy, 3,7-dimethyloctyloxy, and dodecyloxy.

The group represented by R' is preferably alkyl group, aryl group, and aralkyl group, and more preferably alkyl group.

The group represented by R'' is preferably a hydrogen atom, alkyl group, aryl group, and aralkyl group, and more preferably alkyl group.

The compound represented by the general formula (2) is specifically exemplified with a compound that, in the above-mentioned formulas (1A-1 to 1A-10, 1B-1 to 1B-7, 2A-1 to 2A-17, 2B-1 to 2B-14, 2C-1 to 2C-12, 2D-1 to 2D-7, 2E-1 to 2E-6, and 2F-1 to 2F-2), at least 2 of Rs represent a hydrogen atom respectively, and a compound that 2 or more compounds selected from these compounds are bonded through X.

Aromatic compounds having a bonding X in the formula (2) include, for example, the following formulas (3A-1 to 3A-13):

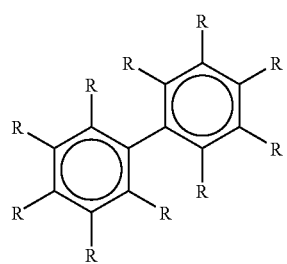

3A-1

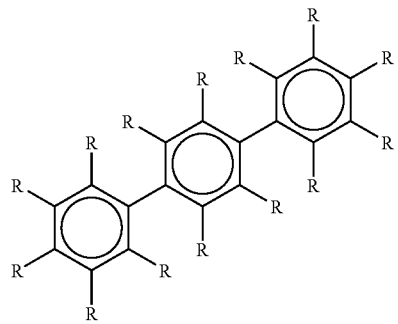

3A-2

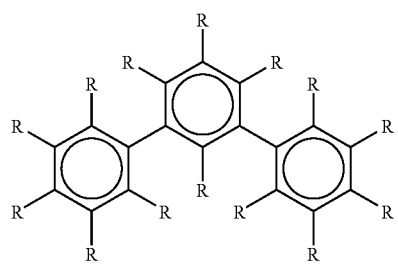

3A-3

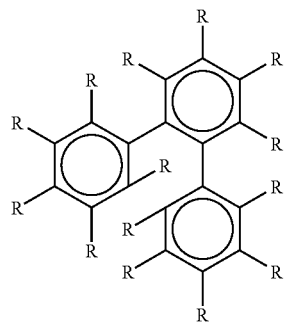

3A-4

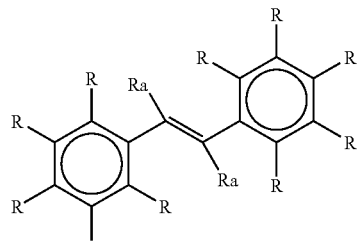

3A-5

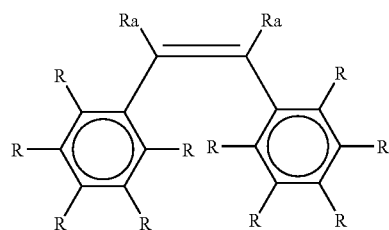

3A-6

3A-7

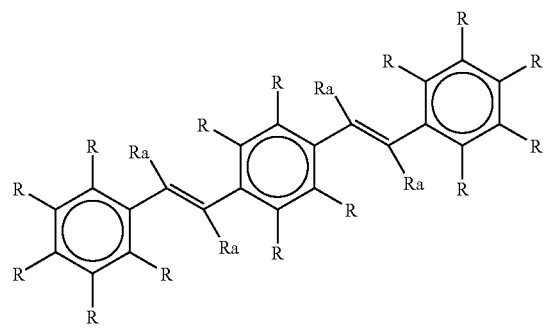

3A-8

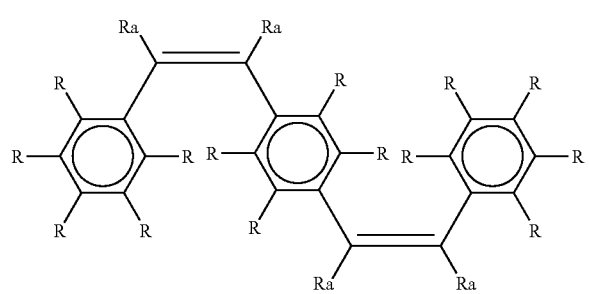

3A-9

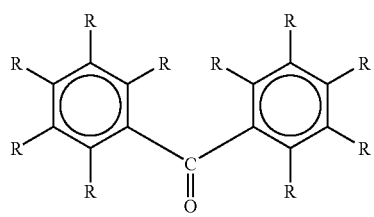

3A-10

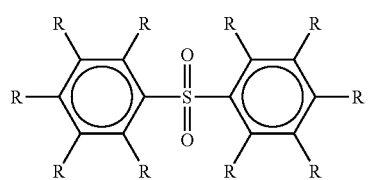

3A-11

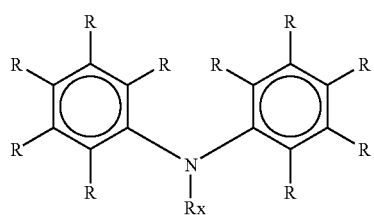

3A-12

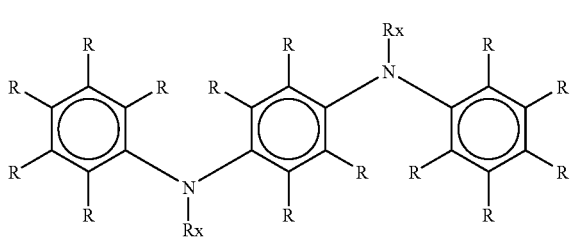

3A-13

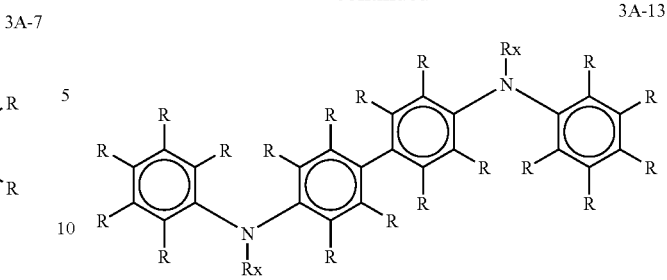

(wherein R, Ra, and Rx represent the same meaning mentioned above).

The aromatic compound used in the invention preferably includes compounds represented by the formulas (1A-1 to 1A-10, 1B-4 to 1B-7, 2C-1 to 2C-12, 2D-1 to 2D-7, 2E-1 to 2E-6, 2F-1 to 2F-2, and 3A-1 to 3A-13), more preferably (1A-1 to 1A-10, 1B-4 to 1B-7, 2C-11 to 2C-12, 2D-1 to 2D-5, 2E-1 to 2E-6, 2F-1 to 2F-2, 3A-1 to 3A-4, and 3A-11 to 3A-13), and particularly preferably (1A-1 to 1A-10, 1B-1 to 1B-2, 1B-4 to 1B-7, 2D-2 to 2D-5, 2E-1 to 2E-3, 2E-6, 2F-1 to 2F-2, and 3A-1 to 3A-4).

The compounds represented by the general formula (2) specifically include, for example, m-xylene, p-xylene, 1,3-dibutylbenzene, 1,4-dibutylbenzene, 1,2-dimethoxybenzene, 1,3-dimethoxybenzene, 1,4-dimethoxybenzene, 1,4-dibutoxybenzene, 1,4-bis(ethylmercapto)benzene, 4-trimethylsilylanisole, 4-methoxybenzenesulfonic acid, triphenylamine, 4-(diphenylamino)benzaldehyde, N,N'-bis(3-methylphenyl)-N,N'-diphenylbenzidine, 2,6-diethylnaphthalene, 2,6-di-t-butylnaphthylene, 1,5-dioctyloxynaphthalene, 2,3-dioctyloxynaphthalene, 2,6-dioctyloxynaphthalene, 1,5-bis(butylthio)naphthalene, 1,4-bis(trimethylsilyl)naphthalene, 1-sulfonic acid methylnaphthalene, 1-phosphonic acid methylnaphthalene, 1,5-bis(4-sulfonic acid butyloxy)naphthalene, 1-(4-nitrophenyl)naphthalene, 1-(4-nitrophenoxy)naphthalene, 1-(4-nitrophenylmethyl)naphthalene, 1-(4-nitrophenylmethyloxy)naphthalene, 1-nitro-6,7-dioctyloxynaphthalene, 2,3-dibutoxyanthracene, 2,6-dibutoxyanthracene, 9,10-dibutoxyphenanthrene, 9,10-dioctyloxyphenanthrene, 3,6-dibutoxyphenanthrene, 3,6-dioctyloxyphenanthrene, 5-nitrobenzo[c]phenanthrene, 1-methylpyrene, 2,7-dimethoxybiphenylene, 1,4,5,8-tetrabutoxybiphenylene, 1,4,5,8-tetraoctyloxybiphenylene, 2,2',5,5'-tetramethoxybiphenyl, 9,10-dibutoxy-9,10-dimethyl-9,10-dihydrophenanthrene, 9,10-dimethyl-9,10-dioctyloxy-9,10-dihydrophenanthrene, 4,5,9,10-tetrahydropyrine, 9,9-dimethylfluorene, 9,9-dipentylfluorene, 9,9-dioctylfluorene, 4-methoxy-7H-benzo[c]fluorene-7-one, 5-bromo-7H-benzo[c]fluorene, 7-methyl-7H-benzo[c]fluorene-7-carboxylic acid methyl ester, 11H-benzo[b]fluorene-11-one, 10-t-butyl-4,5-diphenyl-11H-benzo[b]fluorene, 10-methoxy-7H-dibenzo[b,g]fluorene-7-one, trans-stilbene, cis-stilbene, (Z)-2,3-diphenyl-2,3-butenedinitrile, (E)-2,3-diphenyl-2,3-butenedinitrile, (E)-2,3-diphenylacrylonitrile, (Z)-2,3-diphenylacrylonitrile, 4-butylpyridine, 2,2'-bipyridyl, 6-methylphenanthridine, 6,7-dimethoxyquinoxaline, 6,7-dibutoxyquinoxaline, 2,3-dimethyl-6,7-dimethoxyquinoxaline, 1,5-dioctyloxyisoquinoline, 8-methoxy-4-octyloxyquinoline, 4,8-dioctyloxycinnoline, 2,9-dibutoxybenzo[c]cinnoline, 9,9-dioctyl-1-azafluorene, 9,9-dioctyl-1,8-diazafluorene, 9-methylcarbazol, 3,6-dioctyloxy-9-methylcarbazol, 3,6-dioctyloxy-9-(2,4,6-trimethylphenyl)carbazol, dibenzofuran, 2,8-dioctyloxydibenzofuran, 2,8-dicyclohexylmethyloxydibenzofuran, 4,6- dicyclohexylmethyloxydibenzofuran, 3,7-dioctyloxydibenzofuran, 4,6-dioctyloxydibenzofuran, 2,4,6,8-tetraoctyloxydibenzofuran, dibenzothiophene, 2,8-dioctyloxydibenzothiophene, 2,8-dicyclohexylmethyloxydibenzothiophene, 4,6-dicyclohexylmethyloxydibenzothiophene, 3,7-dioctyloxydibenzothiophene, 4,6-dioctyloxydibenzothiophene, 2,4,6,8-tetraoctyloxydibenzothiophene, dibenzoselenophene, 5-ethyl-5H-dibenzophosphole-5-oxide, 5-benzil-5H-dibenzophosphole, 5-methyl-6(5H)-phenanthridinon, 6,6-dimethyl-6H-dibenzo[b,d]pyran, 6,6-dioctyl-6H-dibenzo[b,d]pyran, 6H-dibenzo[b,d]thiopyran, N-methylpyrrole, N-methyl-3,4-dimethylpyrrole, furan, thiophene, 3-hexylthiophene, 1,1-dimethyl-3,4-diphenylsilole, 4-methyl-1,3-thiazole, 4-ethoxycarbonyl-1,3-thiazole, 1,3-oxazole, 1,3,4-oxadiazole, 4-methoxyfurano[2,3-b]pyridine, 4-methoxythieno[2,3-b]pyridine, 1-methyl-1H-pyrrolo[2,3-b]pyridine, 1-methyl-indole, 4-methoxy-1-methylindole, 4-butylbenzofuran, 2-ethyl-7-methoxybenzofuran, 5-methoxy-2-benzofuransulfonic acid, 2-butyl-1-benzothiophene, 5-methoxy-1-benzothiophene, 3-methoxy-1-benzoselenophene, 2-methoxybenzoxazole, 2-methoxybenzothiazol, 2,1,3-benzothiadiazole, 5,6-dimethyl-2,1,3-benzothiadiazole, and 2,1,3-benzoxadiazol;

preferably m-xylene, p-xylene, 1,3-dibutylbenzene, 1,4-dibutylbenzene, 1,2-dimethoxybenzene, 1,3-dimethoxybenzene, 1,4-dimethoxybenzene, 1,4-dibutoxybenzene, 1,4-bis(ethylmercapto)benzene, 4-trimethylsilylanisole, 4-methoxybenzenesulfonic acid, triphenylamine, 4-(diphenylamino)benzaldehyde, N,N'-bis(3-methylphenyl)-N,N'-diphenylbenzidine, 2,6-diethylnaphthalene, 2,6-di-t-butylnaphthylene, 1,5-dioctyloxynaphthalene, 2,3-dioctyloxynaphthalene, 2,6-dioctyloxynaphthalene, 1,5-bis(butylthio)naphthalene, 1,4-bis(trimethylsilyl)naphthalene, 1-sulfonic acid methylnaphthalene, 1-phosphonic acid methylnaphthalene, 1,5-bis(4-sulfonic acid butyloxy)naphthalene, 1-(4-nitrophenyl)naphthalene, 1-(4-nitrophenoxy)naphthalene, 1-(4-nitrophenylmethyl)naphthalene, 1-(4-nitrophenylmethyloxy)naphthalene, 1-nitro-6,7-dioctyloxynaphthalene, 2,3-dibutoxyanthracene, 2,6-dibutoxyanthracene, 9,10-dibutoxyphenanthrene, 9,10-dioctyloxyphenanthrene, 3,6-dibutoxyphenanthrene, 3,6-dioctyloxyphenanthrene, 5-nitrobenzo[c]phenanthrene, 1-methylpyrene, 2,7-dimethoxybiphenylene, 1,4,5,8-tetrabutoxybiphenylene, 1,4,5,8-tetraoctyloxybiphenylene, 2,2',5,5'-tetramethoxybiphenyl, 9,10-dibutoxy-9,10-dimethyl-9,10-dihydrophenanthrene, 9,10-dimethyl-9,10-dioctyloxy-9,10-dihydrophenanthrene, 4,5,9,10-tetrahydropyrine, 9,9-dimethylfluorene, 9,9-dipentylfluorene, 9,9-dioctylfluorene, 4-methoxy-7H-benzo[c]fluorene-7-one, 5-bromo-7H-benzo[c]fluorene, 7-methyl-7H-benzo[c]fluorene-7-carboxylic acid methyl ester, 11H-benzo[b]fluorene-11-one, 10-t-butyl-4,5-diphenyl-11H-benzo[b]fluorene, 10-methoxy-7H-dibenzo[b,g]fluorene-7-one, trans-stilbene, cis-stilbene, (Z)-2,3-diphenyl-2,3-butenedinitrile, (E)-2,3-diphenyl-2,3-butenedinitrile, (E)-2,3-diphenylacrylonitrile, (Z)-2,3-diphenylacrylonitrile, 9-methylcarbazol, 3,6-dioctyloxy-9-methylcarbazol, 3,6-dioctyloxy-9-(2,4,6-trimethylphenyl)carbazol, dibenzofuran, 2,8-dioctyloxydibenzofuran, 2,8-dicyclohexylmethyloxydibenzofuran, 4,6-dicyclohexylmethyloxydibenzofuran, 3,7-dioctyloxydibenzofuran, 4,6-dioctyloxydibenzofuran, 2,4,6,8-tetraoctyloxydibenzofuran, dibenzothiophene, 2,8-dioctyloxydibenzothiophene, 2,8-dicyclohexylmethyloxydibenzothiophene, 4,6-dicyclohexylmethyloxydibenzothiophene, 3,7-dioctyloxydibenzothiophene, 4,6-dioctyloxydibenzothiophene, 2,4,6,8-tetraoctyloxydibenzothiophene, dibenzoselenophene, 5-ethyl-5H-dibenzophosphole-5-oxide, 5-benzil-5H-dibenzophosphole, 5-methyl-6(5H)-phenanthridinon, 6,6-dimethyl-6H-dibenzo[b,d]pyran, 6,6-dioctyl-6H-dibenzo[b,d]pyran, 6H-dibenzo[b,d]thiopyran, 2-methoxy-1,3-benzoxazole, 2-methoxy-1,3-benzothiazole, 2,1,3-benzothiadiazole, 5,6-dimethyl-2,1,3-benzothiadiazole, and 2,1,3-benzoxadiazol;

more preferably m-xylene, p-xylene, 1,3-dibutylbenzene, 1,4-dibutylbenzene, 1,2-dimethoxybenzene, 1,3-dimethoxybenzene, 1,4-dimethoxybenzene, 1,4-dibutoxybenzene, 1,4-bis(ethylmercapto)benzene, 4-trimethylsilylanisole, triphenylamine, 4-(diphenylamino)benzaldehyde, N,N'-bis(3-methylphenyl)-N,N'-diphenylbenzidine, 2,6-diethylnaphthalene, 2,6-di-t-butylnaphthylene, 1,5-dioctyloxynaphthalene, 2,3-dioctyloxynaphthalene, 2,6-dioctyloxynaphthalene, 1,5-bis(butylthio)naphthalene, 1,4-bis(trimethylsilyl)naphthalene, 1,5-bis(4-sulfonic acid butyloxy)naphthalene, 1-(4-nitrophenyl)naphthalene, 1-(4-nitrophenoxy)naphthalene, 1-(4-nitrophenylmethyl)naphthalene, 1-(4-nitrophenylmethyloxy)naphthalene, 2,3-dibutoxyanthracene, 2,6-dibutoxyanthracene, 9,10-dibutoxyphenanthrene, 9,10-dioctyloxyphenanthrene, 3,6-dibutoxyphenanthrene, 3,6-dioctyloxyphenanthrene, 1-methylpyrene, 2,7-dimethoxybiphenylene, 1,4,5,8-tetrabutoxybiphenylene, 1,4,5,8-tetraoctyloxybiphenylene, 2,2',5,5'-tetramethoxybiphenyl, 9,10-dibutoxy-9,10-dimethyl-9,10-dihydrophenanthrene, 9,10-dimethyl-9,10-dioctyloxy-9,10-dihydrophenanthrene, 4,5,9,10-tetrahydropyrine, 9,9-dimethylfluorene, 9,9-dipentylfluorene, 9,9-dioctylfluorene, 5-bromo-7H-benzo[c]fluorene, 7-methyl-7H-benzo[c]fluorene-7-carboxylic acid methyl ester, 10-t-butyl-4,5-diphenyl-11H-benzo[b]fluorene, trans-stilbene, cis-stilbene, (Z)-2,3-diphenyl-2,3-butenedinitrile, (E)-2,3-diphenyl-2,3-butenedinitrile, (E)-2,3-diphenylacrylonitrile, (Z)-2,3-diphenylacrylonitrile, 9-methylcarbazol, 3,6-dioctyloxy-9-methylcarbazol, 3,6-dioctyloxy-9-(2,4,6-trimethylphenyl)carbazol, dibenzofuran, 2,8-dioctyloxydibenzofuran, 2,8-dicyclohexylmethyloxydibenzofuran, 4,6-dicyclohexylmethyloxydibenzofuran, 3,7-dioctyloxydibenzofuran, 4,6-dioctyloxydibenzofuran, 2,4,6,8-tetraoctyloxydibenzofuran, dibenzothiophene, 2,8-dioctyloxydibenzothiophene, 2,8-dicyclohexylmethyloxydibenzothiophene, 4,6-dicyclohexylmethyloxydibenzothiophene, 3,7-dioctyloxydibenzothiophene, 4,6-dioctyloxydibenzothiophene, 2,4,6,8-tetraoctyloxydibenzothiophene, dibenzoselenophene, 5-benzil-5H-dibenzophosphole, 6,6-dimethyl-6H-dibenzo[b,d]pyran, 6,6-dioctyl-6H-dibenzo[b,d]pyran, 6H-dibenzo[b,d]thiopyran, 2-methoxy-1,3-benzoxazole, 2-methoxy-1,3-benzothiazole, 2,1,3-benzothiadiazole, 5,6-dimethyl-2,1,3-benzothiadiazole, and 2,1,3-benzoxadiazol;

and even more preferably 1,2-dimethoxybenzene, 1,3-dimethoxybenzene, 1,4-dimethoxybenzene, 1,4-dibutoxybenzene, 1,4-bis(ethylmercapto)benzene, 4-trimethylsilylanisole, triphenylamine, N,N'-bis(3-methylphenyl)-N,N'-diphenylbenzidine, 1,5-dioctyloxynaphthalene, 2,3-dioctyloxynaphthalene, 2,6-dioctyloxynaphthalene, 1,5-bis(butylthio)naphthalene, 1,4-bis(trimethylsilyl)naphthalene, 2,3-dibutoxyanthracene, 2,6-dibutoxyanthracene, 9,10-dibutoxyphenanthrene, 9,10-dioctyloxyphenanthrene, 3,6-dibutoxyphenanthrene, 3,6-dioctyloxyphenanthrene, and 2,2',5,5'-tetramethoxybiphenyl.

The aromatic compound used as a raw material for the production method of the invention preferably has a peak potential of 3.50 [V] or less at the oxidation side of an oxidation-reduction potential based on oxidation-reduction potential of ferrocene/ferrocenium ion measured with a cyclic voltammetry for a solution containing the aromatic compound, more preferably 3.00 [V] or less, more preferably 2.60 [V] or less, and particularly preferably 2.00 [V] or less. The lower limit of the peak potential is not particularly limited, preferably 0.00 [V] or more, more preferably 0.30 [V] or more, even more preferably 0.50 [V] or more, and particularly preferably 0.60 [V] or more.

The aromatic compound as a raw material in the invention may be homo-polymerized by utilizing one kind selected from the compounds represented by the general formula (2) or co-polymerized by utilizing 2 or more kinds selected therefrom. When 2 or more kinds of the compounds are co-polymerized, a molar ratio thereof is not particularly limited. Furthermore, since the production method of the invention can obtain a polymer in a relatively favorable yield in spite of the kind of the aromatic compound used as a raw material, applying the method to copolymerization will give an advantage of copolymer composition controllability.

The catalyst employed for the invention is a catalyst composed of a transition metal complex or prepared from a transition metal complex and activating agent.

The catalyst employed for the invention shall have a parameter P of 0.50 or more, the parameter P being defined by the following formula (A)

$$P=Af/Ai \qquad (A)$$

wherein Ai represents an absorbance at an absorption maximum belonging in an absorption band located at the longest wavelength side in an absorption spectrum obtained for a solution containing the catalyst, under a ultraviolet to near-infrared wavelength region from 200 nm to 800 nm, and Af represents an absorbance at the same wavelength applied to the Ai, in an absorption spectrum in the above wavelength region obtained for a solution prepared by adding 3 equivalent of water per mole of the metal contained in the catalyst to the solution.

The parameter P is more preferably 0.55 or more, even more preferably 0.70 or more, and particularly preferably 0.80 or more.

A method for determining the parameter P is explained as follows.

The parameter P is calculated from formula (A) after measuring values of Ai and Af in formula (A).

Specifically, under an inert gas atmosphere at 20 to 30° C., a catalyst (being the transition metal complex when the catalyst is composed of a transition metal complex, or being the transition metal complex and activating agent when the catalyst is composed of a transition metal complex and activating agent) is dissolved in an organic solvent and then agitated for 3 hours to prepare a solution containing the catalyst, an absorption spectrum is measured for thus prepared solution under a ultraviolet to near-infrared wavelength region from 200 nm to 800 nm, and then an absorbance at an absorption maximum belonging in an absorption band located at the longest wavelength side is determined to be a value of Ai (wherein an absorption peak derived from the organic solvent used for preparing the solution is exclude).

Thereafter, into the solution, one equivalent of water per mole of a transition metal atom contained in the transition metal complex dissolved in preparing the solution is added and then agitated for 1 hour, followed by addition of the same amount of water and then agitation for 1 hour, and further followed by addition of the same amount of water and then agitation for 1 hour (consequently, the sum of water added is 3 equivalent of water per mole of a transition metal atom contained in the transition metal complex dissolved in preparing the solution), an absorption spectrum is measured for thus obtained solution under a ultraviolet to near-infrared wavelength region from 200 nm to 800 nm, and then an absorbance at the same wavelength applied to determining the Ai is determined to be the value of Af (wherein an absorption peak derived from the organic solvent used for preparing the solution is exclude).

The preparation of the solution of the catalyst and determination of the absorption spectrum are carried out under an inert gas atmosphere at 20 to 30° C.

The absorption spectrum of the catalyst can be obtained by subtracting the absorption spectrum of the solvent used for preparing the solution from the absorption spectrum of the solution prepared by dissolving the catalyst into the organic solvent.

There is a possibility that a catalyst solution for measuring the absorbance Ai is contaminated with a water accompanied with a solvent and catalyst in preparing the catalyst solution. If an amount of the water is too much, water resistivity of the catalyst may be over-evaluated; however, if being 2.5 or less equivalent of water per mole of a metal contained in the catalyst, the parameter (P) can be evaluated rightly.

An optical path length in measuring an absorption spectrum is 1.0 mm.

The solvent used for preparing the catalyst solution is not particularly limited as long as being an organic solvent capable of dissolving the catalyst, preferably nitrobenzene, chlorobenzene, o-dichlorobenzene, nitromethane, dichloromethane, 1,2-dichloroethane, chloroform, 1,1,2,2-tetrachloroethane, and more preferably nitrobenzene.

When the measurement of spectrum is difficult because a an absorption maximum peak of the catalyst is overlapped with an absorption peak derived from the solvent, selection of a halogenated solvent having low absorption such as dichloromethane is desired. The catalyst solvent is prepared in a concentration for containing Ai value of a catalyst in a range of 0.1 to 1.5.

The catalyst employed for the invention shall have a parameter Eo of 0.50 [V] or more, the parameter Eo being defined by the following formula (B)

$$Eo=(Epa+Epc)/2[V] \qquad (B)$$

(wherein, Epa represents a peak potential at the oxidation side of an oxidation-reduction potential derived from the transition metal contained in the catalyst, at a potential of 0.50 [V] or more based on oxidation-reduction potential of ferrocene/ferrocenium ion measured with a cyclic voltammetry for the solution containing the catalyst, and Epc represents a peak potential at the reduction side corresponding to Epa by the same measurement).

The parameter Eo is a parameter representing an redox pair composed of Epa and Epc, and the value thereof is preferably 0.60 [V] or more, and more preferably 0.70 [V] or more. Furthermore, the upper limit thereof is not particularly limited, desirably lower than the potential oxidizing a solvent used for polymerization reaction, preferably 3.00 [V] or less, and more preferably 2.60 [V] or less.

When, in the catalyst used in the invention, there exist a plurality of redox pairs derived from the transition metal contained in the catalyst, the lowest among redox pairs having 0.50 (V) or more based on oxidation-reduction potential of ferrocene/ferrocenium ion is employed as a parameter Eo. When no redox pair belongs in the above potential range, the highest among redox pair potentials having 0.50 [V] or less is employed as a parameter Eo. When there exists a redox pair having a potential higher than the parameter Eo, the potential thereof is preferably 0.70 [V] or more, more preferably 0.80 [V] or more, and more preferably 0.90 [V] or more. Furthermore, the upper limit thereof is not particularly limited, desirably lower than the potential oxidizing a solvent used for polymerization reaction, preferably 3.00 [V] or less, and more preferably 2.60 [V] or less.

A catalyst solution for measurement is prepared, after the preparation of a degassed solution containing 0.1 mol/L of supporting electrolyte, by dissolving a catalyst with an amount of 1 to 100 mmol/L in terms of the concentration of the transition metal contained in the catalyst at 20 to 30° C. under an inert gas atmosphere. In view of solubility and measurement accuracy at measuring, the transition metal concentration is preferably 2 to 20 mmol/L.

When an activating agent is used in preparing the catalyst, measuring an oxidation-reduction potential of the activated catalyst sometimes becomes difficult because an oxidation-reduction potential derived from non-activated catalyst is measured at measuring a parameter Eo. In this case, anhydrous trifluoroacetic acid as a dehydrating agent may be added in an amount of 0.01 to 2.00 mol/L to the catalyst solution being prepared for measurement.

The supporting electrolyte to be used includes quaternary ammonium salts such as tetra-n-butylammoniumhexafuluorophosphate and tetra-n-butylammoniumtrifuluoromethanesulfonate. When using an activating agent for preparing the catalyst, a preferable supporting electrolyte is the supporting electrolyte of which counter ion is same as the counter ion included in the activating agent to be used. A solvent is not particularly limited as long as being capable of dissolving a supporting electrolyte and catalyst, preferably nitrobenzene, nitromethane, and acetonitrile, and more preferably nitrobenzene.

Measurement for cyclic voltammetry is not particularly limited as long as a measuring system having a potential window corresponding to an oxidation-reduction potential of the catalyst, preferably using a platinum electrode as a working electrode, a platinum electrode as a counter electrode and a silver/silver ion electrode as a reference electrode. A sweep rate of potential is preferably 10 to 500 mV/sec. A measuring range is preferably, based on oxidation-reduction potential of ferrocene/ferrocenium ion, 0.00 [V] or more and the potential oxidizing a solvent used for a measurement or less.

The potential obtained by the measurement of cyclic voltammetry is calibrated based on the oxidation-reduction potential of ferrocene/ferrocenium ion which is obtained by measuring a solution prepared in the same manner by using ferrocene in place of transition metal complex constituting the catalyst.

The transition metal complex includes a catalyst composed of the 3 to 12 group transition metal atoms in the periodic table (IUPAC Nomenclature of Inorganic Chemistry, revised edition, 1989) or a catalyst composed of a ligand and the 3 to 12 group transition metal atoms which are bonded with a group such as =O. The complex may use a complex synthesized in advance or be formed in a reaction system. In the invention, the complex may is used alone or as a mixture of 2 or more kinds thereof.

Among the 3 to 12 group transition metal atoms, preferably are the transition metal atoms in the first transition atom series, more preferably vanadium, chromium, manganese, iron, cobalt, nickel, and copper, and most preferably vanadium. The valence number of the transition metal metals may be appropriately selected from those typically found in nature.

The ligand, as described in ENCYCLOPEDIC DICTIONARY OF CHEMISTRY (the first edition, TOKYO KAGAKU DOJIN, 1989), includes a molecule or ion coordinating to an atom with a coordinate linkage. The atom directly involved in the coordination is call as a coordinating atom. For example, bi-, quadric- or penta-dentate ligand are ligands having 2, 4, or 5 coordinating atoms respectively. In the invention, the coordinating atoms are preferably nitrogen atom, oxygen atom, phosphorus atom, and sulfur atom. The ligand itself may be a neutral molecule or an ion.

The ligands specifically include a neutral molecule or anion obtained by removing one or more proton(s) from the neutral molecule: the neutral molecules being pyridine, 2,6-dimethylpyridine, quinoline, 2-methylquinoline, ethyleneglycol, 1,2-propanediol, 1,3-propanediol, 1,2-butanediol, 2,3-butanediol, 2,3-dimethyl-2,3-butanediol, 1,2-cyclohexanediol, 1,2-ethanedithiol, 1,3-propanedithiol, catechol, hydroxyacetic acid, 2-hydroxypropionic acid, 2-hydroxybutyric acid, hydroxyacetic acid ethyl ester, hydroxyacetone, 2-ketopropionic acid, 2-ketobutyric acid, 2-ketopropionic acid ethyl ester, 1,3-diphenyl-1,3-propanedione, 2,3-butanedione, acetyl acetone, 1,1,1,5,5,5-hexafluoro-2,4-pentanedione, 3,4-hexanedione, 2,5-dimethyl-3,4-hexanedione, 2,2-dimel-3,4-hexanedione, 2,2,5,5-tetramethyl-3,4-hexanedione, 1,2-cyclohexanedione, 2-(N-methylimino)-3-butanone, 2-(N-ethylimino)-3-butanone, 2-(N-propylamino)-3-butanone, 2-(N-butylimino)-3-butanone, 2-(N-phenylimino)-3-butanone, 3-(N-methylimino)-3-hexanone, 2-(N-methylimino)-cyclohexanone, 2-(N-methylimino)-propionic acid methyl ester, 2-(N-methylimino)-butyric acid ethyl ester salicylaldehyde, salicylic acid, ethyl acetoacetate, oxalic acid, malonic acid, diethyl malonate, glycine, alanine, valine, leucine, phenylalanine, monoethanolamine, 3-amino-1-propanol, 2-amino-1-propanol, 1-amino-2-propanol, 3-amino-2-butanol, 3-amino-2,3-dimethyl-2-butanol, 2-amino-1-cyclohexanol, N-methylethanolamine, N-ethylethanolamine, N-propylethanolamine, N-butylethanolamine, N-phenylethanolamine, N-methylpropanolamine, N-phenylpropanolamine, N,N-dimethylethanolamine, N,N-diethylethanolamine, N-salicylidenemethylamine, N-salicylideneethylamine, N-salicylidenepropylamine, N-salicylidenebutylamine, N-salicylideneaniline, 4-(N-methylimino)-2-pentanone, 4-(N-ethylimino)-2-pentanone, 4-(N-propylamino)-2-pentanone, 4-(N-phenylimino)-2-pentanone, 2-(N-methylimino) propionic acid, 3-(N-methylimino)propionic acid, 3-(N-methylimino)propionic acid ethyl ester, 2-(N-methylimino) butyric acid, 2-(N-methylimino)propanol, 1,2,3-trihydroxypropane, 3-formyl-salicylic acid, diethylenetriamine, 4-(2-hydroxyethylamino)-2-pentanone, N-salicylidene-2-hydroxyaniline, tris(2-pyridylmethyl) amine, tris(2-imidazolylmethyl)amine, tris(1-methyl-2-imidazolylmethyl)amine, tris(2-benzimidazolylmethyl)amine, tris(2-benzoxazolylmethyl)amine, tris(2-benzthiazolilmethyl)amine, tris(1-pyrazolylmethyl)amine, tris(3,5-dimethyl-1-pyrazolylmethyl)amine, tris(3,5-dipropyl-1-pyrazolylmethyl)amine, tris(3,5-diphenyl-1-pyrazolylmethyl) amine, nitrilotriacetic acid, nitrilotriethanol, nitrilotri-1-propanol, tris(2-pyridyl-2-ethyl)amine, tris(1-pyrazolyl-2-ethyl)amine, N-(2-mercaptoethyl)-N,N-diethanolamine, N-(diphenylphosphinoethyl)-N,N-diethanolamine, triethyleneglycol, tripropyleneglycol, triethylenetetramine, N,N'''-dimethyltriethylenetetramine, N,N,N''',N'''-tetramethyltriethylenetetramine, N,N'-bis(2-hydroxyethyl) ethylenediamine, N,N'-bis(3-hydroxypropyl) ethylenediamine, N,N'-ethylenediamine diacetic acid, N,N'-bis(2-pyridylmethyl)ethylenediamine, N,N'-bis(2-imidazolylmethyl)ethylenediamine, N,N'-bis(2-benzimidazolylmethyl)ethylenediamine, N,N'-bis(2- mercaptoethyl)ethylenediamine, N,N'-bis(diphenylphosphinoethyl)ethylenediamine, N,N'-disalicylideneethylenediamine, N,N'-bis(1-methyl-3-oxobutylidene)ethylenediamine, N-2-hydroxyethyl-N'-salicylideneethylenediamine, N-2-hydroxyethyl-N'-salicylidene-1,3-propylenediamine, N-3-hydroxypropyl-N'-salicylidene-1,3-propylenediamine, N-3-hydroxypropyl-N'-salicylideneethylenediamine, N-2-dimethylaminoethyl-N'-salicylideneethylenediamine, N-2-pyridylmethyl-N'-salicylideneethylenediamine, N,N'-bis(2-amino-3-benzylidene)ethylenediamine, 1-(diacetylmonooximeimino)-3-(diacetylmonooximatoimino)propane, 12-crown-4,1,4,8,11-tetraazacyclotetradecane, 1,4,8,11-tetraazacyclotetradecane-5,7-dione, 1,4,8,11-tetramethyl-1,4,8,11-tetraazacyclotetradecane, 1,4,7,10-tetrathiacyclododecane, 2,3,9,10-tetramethyl-1,4,8,11-tetraazacyclotetradeca-1,3,8,10-tetraene, 1,13-tetraene, porphyrin, 5,10,15,20-tetraphenylporphyrin, octaethylporphyrin, phthalocyanine, m-xylenebis(acetylacetone), and 5-t-butyl-m-xylenebis(acetylacetone).

The transition metal complex used in the invention may require a counter ion to maintain an electrical neutrality thereof. A conjugated base of the Broensted acid is typically used as the counter anion, specifically includes fluoride ions, chloride ions, bromide ions, iodide ions, sulfate ions, nitrate ions, carbonate ions, perchlorate ions, tetrafluoroborate ions, hexafluorophosphate ions, methanesulfonate ions, trifluoromethanesulfonate ions, toluenesulfonate ions, acetate ions, trifluoroacetate ions, propionate ions, benzoate ions, hydroxide ions, oxide ions, methoxide ions, ethoxide ions, and the like. As a counter cation, cations of alkali metals and alkaline earth metals are appropriately used.

The transition metal complex catalyst of the invention may be coordinated with a solvent and the like in a step of synthesizing a raw material of the complex and/or a step of oxidative polymerization.

The transition metal complex is preferably a vanadium complex, specifically exemplified with a vanadium mono-nuclear complex such as vanadium tris(acetylacetonato), vanadyl bis(acetylacetonato), vanadyl bis(1,1,1,5,5,5-hexafluoro-2,4-pentanedionato), and vanadyl bis(1-phenyl-1,3-butanedionato); and a vanadium di-nuclear complex represented by the general formula (1), and, in view of the catalytic activity, preferably the vanadium di-nuclear complex represented by the general formula (1):

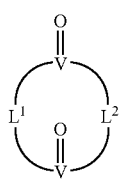

(1)

wherein $L^1$ and $L^2$ represent a ligand having 4 or more coordinating atoms respectively and connect to two vanadium atoms with a coordinating atom respectively. The $L^1$ and $L^2$ may be same or different each other.

The $L^1$ and $L^2$ in the general formula (1) are a ligand having 4 or more coordinating atoms for bridging the two vanadium atoms respectively.

The vanadium di-nuclear complex represented by the general formula (1) includes more preferably a vanadium di-nuclear complex represented by the general formula (1-2):

(1-2)

wherein $V^1$ and $V^2$ represent a vanadium atom respectively, $L^3$ and $L^4$ represent a ligand having 4 or more coordinating atoms respectively and connect to two vanadium atoms with a coordinating atom respectively, wherein the number of bondings interposing between the coordinating atoms in $L^3$ coordinating to $V^1$ and the coordinating atoms in $L^3$ coordinating to $V^2$, and the number of bondings interposing between the coordinating atoms in $L^4$ coordinating to $V^1$ and the coordinating atoms in $L^4$ coordinating to $V^2$ are 6 or more respectively (i.e. the minimum number of the bondings for interposition is 6). Furthermore, the $L^3$ and $L^4$ may be same or different from each other.

In $L^3$ and $L^4$, the minimum number of the bondings interposing between the coordinating atoms coordinating to $V^1$ and $V^2$ in the respective ligands is preferably 6 to 30, more preferably 7 to 20, and particularly preferably 8 to 17.

The specific examples of $L^3$ and $L^4$ include, for example, 2,2'-[1,3-phenylenebis(methylene)]bisacetacetic acid, 2,2'-[1,3-phenylenebis(methylene)]bis(3-dimethylaminopropanol), 3,3'-[1,3-phenylenebis(methylene)]bis(2,4-pentanedione), 3,3'-[(5-t-butyl-1,3-phenylenebis(methylene)]bis(2,4-pentanedione), 2,2'-[1,3-phenylenebis(methylene)]bis(1,3-diphenyl-1,3-propanedione), 3,3'-[2,7-naphthalenediylbis(methylene)]bis(2,4-pentanedione), 3,3'-[1,8-anthracenediylbis(methylene)]bis(2,4-pentanedione) 3,3'-[1,8-anthracenediylbis(methylene)]bis(1,1,1,3,3,3-hexafluoro-2,4-pentanedione), 3,3'-[2,6-pyridinediylbis(methylene)]bis(2,4-pentanedione), 2,2'-[2,6-pyridinediylbis(methylene)]bis(1,1,1,3,3,3-hexafluoro-2,4-pentanedione), 3,3'-[1, 8-anthracenediylbis(methylene)]bis(1,1,1,3,3,3-hexafluoro-4-imino-2-pentanone), and 2,2'-[2,6-pyridinediylbis (methylene)]bis(1,1,1,3,3,3-hexafluoro-4-imino-2-pentanone).

The specific examples of vanadium di-nuclear complex represented by the general formula (1-2) include, for example, bis-μ-(2,2'-[1,3-phenylenebis(methylene)]bis(3-N,N-dimethyl aminopropyloxy))divanadium oxide and a vanadium di-nuclear complex represented by the general formula (1-3), and preferably a vanadium di-nuclear complex represented by the general formula (1-3):

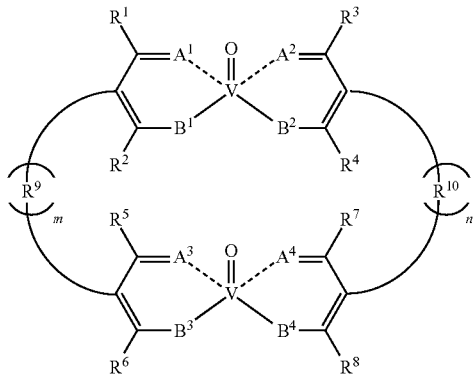

(1-3)

wherein $A^1$, $A^2$, $A^3$ and $A^4$ each independently represent an oxygen atom, or $NR^{11}$, and $B^1$, $B^2$, $B^3$ and $B^4$ each independently represent —O— or —$NR^{12}$—; $R^1$, $R^2$, $R^3$, $R^4$, $R^5$, $R^6$, $R^7$ and $R^8$ each independently represent optionally substituted hydrocarbon group or optionally substituted hydrocarbonoxy group; $R^9$ and $R^{10}$ each independently represent optionally substituted alkylene group, optionally substituted arylene group, —O—, —S—, —$SO_2$— or —$NR^{13}$—, and when $R^9$ and $R^{10}$ exist in a plural number respectively, they may be same or different each other; m and n each independently represent an integer of 1 to 7; $R^{11}$, $R^{12}$ and $R^{13}$ each independently represent a hydrogen atom or optionally substituted hydrocarbon group; when $R^{11}$, $R^{12}$ and $R^{13}$ exist in a plural number respectively, they may be same or different each other; when both of $A^1$ and $A^2$ and/or both of $A^3$ and $A^4$ are together $NR^{11}$ respectively, two $R^{11}$s may combine to form divalent hydrocarbon group and connect $A^1$ and $A^2$ and/or $A^3$ and $A^4$ each other; and when both of $B^1$ and $B^2$ and/or both of $B^3$ and $B^4$ are together —$NR^{12}$— respectively, two $R^{12}$s may combine to form divalent hydrocarbon group and connect $B^1$ and $B^2$ and/or $B^3$ and $B^4$ each other.

$R^1$, $R^2$, $R^3$, $R^4$, $R^5$, $R^6$, $R^7$ and $R^8$ in the general formula (1-3) each independently represent optionally substituted hydrocarbon group or optionally substituted hydrocarbonoxy group.

The hydrocarbon group of $R^1$, $R^2$, $R^3$, $R^4$, $R^5$, $R^6$, $R^7$ and $R^8$ in the general formula (1-3) includes, for example, linear, branched and cyclic alkyl groups having about 1 to 50 total carbon atoms such as methyl group, ethyl group, propyl group, isopropyl group, butyl group, isobutyl group, t-butyl group, pentyl group, cyclopentyl group, hexyl group, cyclohexyl group, norbornyl group, nonyl group, decyl group, and 3,7-dimethyloctyl group; aryl groups having about 6 to 60 total carbon atoms such as phenyl group, 4-methylphenyl group, 4-isopropylphenyl group, 4-butylphenyl group, 4-t-butylphenyl group, 4-hexylphenyl group, 4-cyclohexylphenyl group, 4-adamantylphenyl group, 4-phenylphenyl group, 1-naphthyl group, and 2-naphthyl group; and aralkyl groups having about 7 to 50 total carbon atoms such as phenylmethyl group, 1-phenylethyl group, 2-phenylethyl group, 1-phenyl-1-propyl group, 1-phenyl-2-propyl group, 2-phenyl-2-propyl group, 1-phenyl-3-propyl group, 1-phenyl-4-butyl group, 1-phenyl-5-pentyl group, and 1-phenyl-6-hexyl group.

The hydrocarbon group is preferably a hydrocarbon group having 1 to 30 carbon atoms, more preferably a hydrocarbon group having 1 to 22 carbon atoms, and even more preferably a hydrocarbon group having 1 to 16 carbon atoms.

The hydrocarbon group may be substituted with alkoxy group, nitro group, cyano group, and a halogen atom.

The alkoxy group includes, for example, alkoxy groups having about 1 to 50 carbon atoms such as methyloxy group, ethyloxy group, propyloxy group, isopropyloxy group, butyloxy group, isobutyloxy group, t-butyloxy group, and pentyloxy group.

The halogen atom includes a fluorine atom, a chlorine atom, a bromine atom, and an iodine atom The hydrocarbonoxy group of $R^1$, $R^2$, $R^3$, $R^4$, $R^5$, $R^6$, $R^7$ and $R^8$ in the general formula (1-3) includes, for example, linear, branched and cyclic alkoxy groups having about 1 to 50 total carbon atoms such as methyloxy group, ethyloxy group, propyloxy group, isopropyloxy group, butyl oxy group, isobutyloxy group, t-butyloxy group, pentyloxy group, hexyloxy group, and cyclohexyloxy group; aryloxy groups having about 6 to 60 total carbon atoms such as phenoxy group, 4-methylphenoxy group, 4-propylphenoxy group, 4-isopropylphenoxy group, 4-butylphenoxy group, 4-t-butylphenoxy group, 4-hexylphenoxy group, 4-cyclohexylphenoxy group, 4-phenoxyphenoxy group, 1-naphthyloxy group, and 2-naphthyloxy group; and aralkyloxy groups having about 7 to 60 total carbon atoms such as phenylmethyloxy group, 1-phenylethyloxy group, 2-phenylethyloxy group, 1-phenyl-1-propyloxy group, 1-phenyl-2-propyloxy group, 2-phenyl-2-propyloxy group, 1-phenyl-3-propyloxy group, 1-phenyl-4-butyloxy group, 1-phenyl-5-pentyloxy group, and 1-phenyl-6-hexyloxy group.

The hydrocarbonoxy group is preferably a hydrocarbonoxy group having 1 to 40 carbon atoms, more preferably a hydrocarbonoxy group having 1 to 30 carbon atoms, and even more preferably a hydrocarbonoxy group having 1 to 20 carbon atoms.

The hydrocarbonoxy group may be substituted with alkoxy group, nitro group, cyano group, and a halogen atom. The alkoxy group and halogen atom include alkoxy groups and halogen atoms exemplified with the substituent of the hydrocarbon group represented by $R^1$ to $R^8$ mentioned above.

$R^9$ and $R^{10}$ each independently represent optionally substituted alkylene group, optionally substituted arylene group, —O—, —S—, —$SO_2$— or —$NR^{13}$—.

The alkylene group of $R^9$ and $R^{10}$ in the general formula (1-3) includes, for example, linear, branched and cyclic alkylene groups having about 1 to 20 total carbon atoms such as methylene group, ethylene group, 1,1-propylene group, 1,2-propylene group, 1,3-propylene group, 2,4-butylene group, 2,4-dimethyl-2,4-butylene group, 1,2-cyclopentylene group, and 1,2-cyclohexylene group.

The alkylene group may be substituted with alkoxy group, nitro group, cyano group, and a halogen atom. The alkoxy group and halogen atom include alkoxy groups and halogen atoms exemplified with the substituent of the hydrocarbon group represented by $R^1$ to $R^8$ mentioned above.

The optionally substituted arylene group of $R^9$ and $R^{10}$ in the general formula (1-3) is a divalent group formed from an aromatic compound by losing 2 hydrogen atoms therefrom.

The aromatic compound includes aromatic compounds having about 6 to 60 total carbon atoms such as benzene, naphthalene, anthracene, tetracene, biphenyl, biphenylene, furan, dibenzofuran, thiophene, dibenzothiophene, and pyridine.

The aromatic group may be substituted with alkyl group, aralkyl group, alkyloxy group, nitro group, cyano group, and a halogen atom.

The alkyl group includes, for example, linear, branched and cyclic alkyl groups having about 1 to 50 carbon atoms such as methyl group, ethyl group, propyl group, isopropyl group, butyl group, isobutyl group, t-butyl group, pentyl group, cyclopentyl group, hexyl group, cyclohexyl group, norbornyl group, nonyl group, decyl group, and 3,7-dimethyloctyl group. The aralkyl group includes, for example, aralkyl groups having about 7 to 50 carbon atoms such as phenylmethyl group, 1-phenylethyl group, 2-phenylethyl group, 1-phenyl-1-propyl group, 1-phenyl-2-propyl group, 2-phenyl-2-propyl group, 1-phenyl-3-propyl group, 1-phenyl-4-butyl group, 1-phenyl-5-pentyl group, and 1-phenyl-6-hexyl group.

The alkoxy group and halogen atom include alkoxy groups and halogen atoms exemplified with the substituent of the hydrocarbon group represented by $R^1$ to $R^8$ mentioned above.

m and n in the general formula (1-3) each independently represent an integer of 1 to 7. m and n are preferably 1 to 5, and more preferably 1 to 3.

When $R^9$ and $R^{10}$ exist in a plural number respectively, they may be same or different from each other $R^{11}$, $R^{12}$ and $R^{13}$ in the general formula (1-3) each independently represent a hydrogen atom or optionally substituted hydrocarbon group. The optionally substituted hydrocarbon group is same as the optionally substituted hydrocarbon group represented by $R^1$ to $R^8$ in the general formula (2).

When $R^{11}$, $R^{12}$ and $R^{13}$ exist in a plural number respectively, they may be same or different each other.

When both of $A^1$ and $A^2$ and/or both of $A^3$ and $A^4$ are together $NR^{11}$ respectively, two $R^{11}$s may combine to represent divalent hydrocarbon group and connect $A^1$ and $A^2$ and/or $A^3$ and $A^4$ each other; and when both of $B^1$ and $B^2$ and/or both of $B^3$ and $B^4$ are together —$NR^{12}$— respectively, two $R^{12}$S may combine to represent divalent hydrocarbon group and connect $B^1$ and $B^2$ and/or $B^3$ and $B^4$ each other.

$A^1$, $A^2$, $A^3$ and $A^4$ are preferably an oxygen atom, and $B^1$, $B^2$, $B^3$ and $B^4$ are preferably —O—.

The divalent hydrocarbon group formed by combining the groups represented by two $R^{11}$s or two $R^{12}$s includes linear, branched and cyclic alkylene groups having about 1 to 20 total carbon atoms such as methylene group, ethylene group, 1,1-propylene group, 1,2-propylene group, 1,3-propylene group, 2,4-butylene group, 2,4-dimethyl-2,4-butylene group, 1,2-cyclopentylene group, and 1,2-cyclohexylene group; and divalent aromatic groups having about 6 to 20 total carbon atoms such as 1,2-phenylene group and 2,3-naphthylene group.

Such divalent hydrocarbon groups may have a substituent including, as examples, optionally substituted hydrocarbon groups, optionally substituted hydrocarbonoxy groups, nitro group, cyano group, and a halogen atom, and specific examples of such substituents are exemplified as done for the substituent of the hydrocarbon group represented by $R^1$ to $R^8$ mentioned above.

The vanadium di-nuclear complex represented by the general formula (1-3) includes, for example, bis-µ-(3,3'-(1,3-phenylenebis(methylene))bis(2,4-pentanedionato))divanadium(IV)oxide, bis-µ-(3,3'-(5-t-butyl-1,3-phenylenebis(methylene))bis(2,4-pentanedionato))divanadium(IV)oxide, bis-µ-(2,2'-(1,3-phenylenebis(methylene))1,3-diphenyl-1,3-propanedionato))divanadium(IV)oxide, bis-µ-(3,3'-(2,7-naphthalenediylbis(methylene))bis(2,4-pentanedionato))divanadium(IV)oxide, bis-µ-(3,3'-(1,8-anthracenediyl)bis(4-imino-2-pentanonato-N,0))divanadium(IV)oxide, and bis-µ-(3,3'-(2,6-pyridyl)bis(4-imino-2-pentanonato-N,0))divanadium(IV)oxide.

The method for synthesizing the vanadium di-nuclear complex in the invention includes, for example, a method described in J. Coord. Chem., 1973, 3, 113.

When using an activating agent together with the transition metal complex for catalyst preparation, the activating agent includes protonic acid or Lewis acid.

The protonic acid includes, for example, protons such as methanesulfonic acid, trifluoromethanesulfonic acid, p-toluenesulfonic acid, trifluoroacetic acid, sulfuric acid, nitric acid, and acetic acid, and preferably methanesulfonic acid, trifluoromethanesulfonic acid, and trifluoroacetic acid. The Lewis acid includes, for example, triphenylmethyltetrafluoroborate, aluminium chloride, and scandium tritriflate, and preferably triphenylmethyltetrafluoroborate.

An amount of an acid used as the activating agent for catalyst preparation is not particularly limited except for interfering polymerization reaction, usually 0.1 to 100.0 equivalent per transition metal complex, preferably 0.5 to 50.0 equivalent, and more preferably 1 to 10.0 equivalent.

The catalyst used in the invention is preferably a catalyst prepared from a vanadium complex and an activating agent.

A method for preparing the catalyst is not particularly limited, usually prepared by adding an activating agent into a vanadium complex in the presence of a solvent. The catalyst may be used for polymerization reaction as the prepared solution itself or as an isolated one.

When the transition metal complex is a vanadium mononuclear complex, an amount of an acid used as the activating agent is preferably more than 2.0 equivalent per the vanadium mononuclear complex, more preferably more than 2.2 equivalent, and even more preferably more than 2.4 equivalent.

When the transition metal complex is a vanadium di-nuclear complex, an amount of an acid used as the activating agent is preferably more than 2.0 equivalent per the vanadium di-nuclear complex, more preferably more than 2.2 equivalent, and even more preferably more than 2.4 equivalent.

In the method of the invention, an amount of the metal contained in the catalyst used for the oxidative polymerization is usually about 0.001 to 50 mole % per aromatic compound as the raw material, preferably 0.01 to 20 mole %, and more preferably 0.05 to 10 mole %.

The catalyst may be used alone or as a mixture of 2 or more kinds thereof.

In the invention, an oxidizing agent is used together with the catalyst.

The oxidizing agent to be used together includes, for example, oxygen, benzoquinone, hydrogen peroxide, t-butylhydroperoxide, di-t-butylperoxide, cumenehydroperoxide, dicumylperoxide, peracetic acid, and perbenzoic acid, and preferably oxygen. The oxygen may be a mixture with an inert gas or an air. When the oxygen is used, it is usually used in over excess being equal to or more than 0.5 equivalent per monomer, but a partial pressure thereof is not limited. When the oxidizing agent other than oxygen is used, it is used usually in an amount of 0.5 to 3 equivalent per aromatic compound used as a monomer. These oxidizing agents may be used alone or as a combination of 2 or more kinds thereof.

The invention can be performed in the absence of a solvent, but usually in the presence of an organic solvent. The organic solvent includes, for example, nitrobenzene, chlorobenzene, o-dichlorobenzene, nitromethane, dichloromethane, and 1,2-dichloroethane, chloroform, and 1,1,2,2-tetrachloroethane. These organic solvent may be used alone or as a mixture of 2 or more kinds thereof.

The organic solvent is usually used in a ratio for adjusting a monomer concentration to 0.1 to 90% by weight. The ratio is preferably 1 to 50% by weight, more preferably 2 to 30% by weight, and even more preferably 5 to 25% by weight.

A temperature for carrying out the oxidative polymerization is not particularly limited as long as being in a range maintaining a reaction medium in a liquid state. The temperature range is preferably −50° C. to 200° C., more preferably 0° C. to 150° C., and more preferably 0° C. to 100° C.

A reaction time varies depending on the reaction conditions including temperatures, usually being 1 hour or more, and preferably 2 to 500 hours.

Post-treatments can be conducted according to the known procedures. For example, the intended polymer can be obtained by adding a lower alcohol such as methanol into a reaction solution to precipitate, collecting the precipitated with a filtration, and then drying.

If the polymer obtained by the above-mentioned post-treatments has low purity, it can be purified by the conventional method such as re-crystallization and a continuous extraction with the Soxhlet extractor.

According to the method of the invention, even if water is present during the polymerization, the corresponding aromatic compound polymer can be produced in a relatively favorable yield.

The invention is effective even if the maximum value of the water (usually, a water content in a reaction mixture at finishing the oxidative polymerization reaction) present in a reaction system from the commencement of polymerization to the finishing is 0.01 mole or more per 1 mole of the metal contained in a catalyst. The maximum value of the water present in a reaction system is preferably 0.05 equivalent or more, more preferably 0.10 equivalent or more, and even more preferably 0.50 equivalent or more. The water is derived from a water contained in a raw material to be used as well as a water generated during polymerizing.

In the invention, the corresponding aromatic compound polymer can be produced in a relatively favorable yield without using the dehydrating agent. Particularly, there have been a possibility that, if a dehydrating agent containing halogen usually represented by anhydrous trifluoroacetic acid is used in a large amount as the dehydrating agent, a halogen atom or a group containing a halogen atom is introduced into a resultant polymer. The present invention is favorable to solve this problem when a dehydrating agent is substantially not used.

Furthermore, when a dehydrating agent is used in the invention, the aromatic compound polymer can be obtained with less amount of the dehydrating agent in favorable yield in comparison with the known production methods.

When a dehydrating agent is used in the invention, the dehydrating agent includes acetic anhydride, anhydrous trifluoroacetic acid, anhydrous trifluoromethanesulfonic acid, and acetylchloride, and preferably anhydrous trifluoroacetic acid.

The aromatic compound polymer produced by the production method of the invention, when using the compound represented by the general formula (2) mentioned above, contains a repeating unit represented by the following general formula (3) in the aromatic compound polymer:

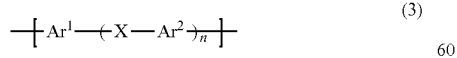
(3)

(wherein $Ar^1$, $Ar^2$, X and n respectively represent the same meaning as mentioned above).

The aromatic compound polymer obtained by the production method of the invention can be used as functional materials such as fluorescent polymer materials, conductive polymer materials and the like.

EXAMPLES

The invention will be explained in more detail according to Examples hereinafter, but should not be construed to be limited thereto.

An absorption spectrum was measured at 25° C. with the Ultraviolet and Visible Spectrophotometer V-530 manufactured by JASCO Corporation with using a quartz cell having an optical path length of 1 mm.

A measurement for cyclic voltammetry was conducted with the Electrochemical Analyzer Model-600A manufactured by ALS with using a platinum electrode as the working electrode, a platinum electrode as the counter electrode and a silver/silver ion electrode as the reference electrode, in a nitrobenzene solution containing 0.1 mol/L of tetra-n-butylammoniumhexafuluorophosphate as the supporting electrolyte or a nitrobenzene solution containing 0.1 mol/L of tetra-n-butylammoniumtrifuluoromethanesulfonate, under a nitrogen atmosphere at 25° C. The potential obtained was used after calibrating the oxidation-reduction potential of ferrocene/ferrocenium ion measured under the same conditions to be 0 [V] (in Examples, referred to as [V vs Fc/Fc+ standard]).

A measurement of water content in a reaction solution was conducted with a Karl Fischer Coulometric titrator AQ-2000 manufactured by HIRANUMA with using HYDRANAL(R) Coulomat AK as the anode solution and HYDRANAL(R) Coulomat CG-K as the cathode solution.

A number average molecular weight (Mn) and weight average molecular weight (Mw) of a polymer were analyzed with a gel permeation chromatography and the number average molecular weight (Mn) and weight average molecular weight (Mw) were determined in terms of standard polystyrene. The analysis was conducted with PL-GPC210 system (RI detector) manufactured by Polymer Laboratories with using 3 columns of PLgel 10 um MIXED-B manufacture by Polymer Laboratories and o-dichlorobenzene (containing 0.01% w/v of 2,6-di-t-butyl-methylphenol) as eluent at 40° C. or 100° C.

Example 1

Polymerization of 1,4-dibutoxybenzene (Parameter P: 0.93, Parameter Eo: 0.90)

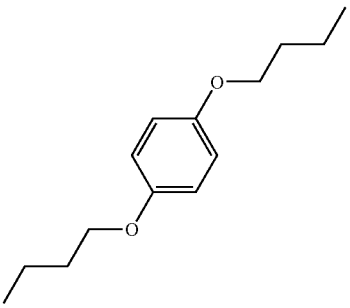

(1,4-dibutoxybenzene) Oxidation side peak potential 0.86 (V Fc/Fc+standard)

31.02 mg (0.042 mmol) of bis-μ-(3,3'-(1,3-phenylenebis(methylene))bis(2,4-pentanedionato))divanadium(IV)oxide was dissolved in 0.34 mL of nitrobenzene and 0.019 mL (0.21 mmol) of trifluoromethanesulfonic acid, and then agitated under an oxygen atmosphere at 25° C. for 1 hour. The solution obtained above was added with a solution composed of 250.2 mg (1.13 mmol) of 1,4-dibutoxybenzene and 0.79 mL of nitrobenzene, and then agitated under the oxygen atmosphere at 25° C. for 55 hours. When a water content was measured after elapsing 1 hour from the commencement of the agitation, the water content in the reaction solution was 3.6 mg (0.20 mmol) and 1.2 equivalent of water per mole of the metal contained in the catalyst was detected. Thereafter, the reaction solution was dropped into a hydrochloric acidic methanol, followed by subjecting the precipitation obtained to filtration, washing, and drying to obtain 44.93 mg of polymer (yield 18.1%). Mn=2400, Mw=4300.

Determination of Parameter P

In a Schlenk flask having 50 cc capacity, 62.15 mg (0.085 mmol) of bis-μ-(3,3'-(1,3-phenylenebis(methylene))bis(2,4-pentanedionato))divanadium(IV)oxide was added, and then the Schlenk flask was sufficiently dried under a reduced pressure, followed by being filled with a dried argon. Under an atmosphere of the dried argon, 40.0 mL of nitrobenzene and 0.0375 mL (0.424 mmol) of trifluoromethanesulfonic acid were added, and then agitated at 25° C. for 3 hours to measure an absorption spectrum. A wavelength of the absorption maximum belonging in the absorption band located at the longest wavelength side was 602 nm, and Ai=0.87214 was determined. A water content contained in the reaction solution at this determination was 2.0 equivalent per mole of vanadium metal.

In the above solution, 0.003 mL (0.17 mmol) of water was added, and then agitated at 25° C. for 1 hour; further adding 0.003 mL (0.17 mmol) of water in the above solution, and then agitating at 25° C. for 1 hour; and then still further adding 0.003 mL (0.17 mmol) of water in the above solution, and then agitating at 25° C. for 1 hour to measure an absorption spectrum. According to the absorbance at the wavelength of 602 nm, Af=0.81517 was determined. According to the above results, the parameter P of the catalyst was determined as 0.93.

Determination of Parameter Eo:

In a measuring flask having a capacity of 50 mL, 1.96 g (5 mmol) of tetra-n-butylammoniumtrifluoromethanesulfonate and 40 mL of nitrobenzene were put in, degassed by bubbling for 30 minutes with the dried argon, added with 111 μL (1.25 mmol) of trifluoromethanesulfonic acid and 0.71 mL (5 mmol) of anhydrous trifluoroacetic acid, and then messed up with nitrobenzene to prepare a supporting electrolyte solution. In 10 mL of this supporting electrolyte solution, under an atmosphere of a dried nitrogen, 73.5 mg (0.10 mmol) of bis-μ-(3,3'-(1,3-phenylenebis(methylene))bis(2,4-pentanedionato))divanadium(IV)oxide was added, maintained at 25° C. for 6 hours, and then subjected to the cyclic voltammetry measurement. This measurement resulted in Epa=0.99 (V Fc/Fc+standard) and Epc=0.80 (V Fc/Fc+standard). According to the above results, the parameter Eo of the catalyst was determined as 0.90 (V).

In this cyclic voltammetry measurement, a redox pair derived from a catalyst not activated at 0.49 (V Fc/Fc+standard) was also observed.

Example 2

Polymerization of 1,4-dibutoxybenzene (Parameter P: 0.58, Parameter Eo: 1.05)

44.69 mg (0.167 mmol) of vanadyl acetylacetonato was dissolved in 0.67 mL of nitrobenzene and 0.037 mL (0.418 mmol) of trifluoromethanesulfonic acid, and then agitated under an oxygen atmosphere at 25° C. for 1 hour. The solution obtained above was added with a solution composed of 500.2 mg (2.24 mmol) of 1,4-dibutoxybenzene and 1.51 mL of nitrobenzene, and then agitated under the oxygen atmosphere at 25° C. for 55 hours. When a water content was measured after finishing the agitation, the water content in the reaction solution was 15.9 mg (0.88 mmol) and 5.2 equivalent of water per mole of the metal contained in the catalyst was detected. Thereafter, the reaction solution was dropped into a hydrochloric acidic methanol, followed by subjecting the precipitation obtained to filtration, washing, and drying to obtain 73.8 mg of polymer (yield 14.9%). Mn=2500, Mw=4300.

Determination of Parameter P

In a Schlenk flask having 50 cc capacity, 44.48 mg (0.168 mmol) of vanadyl acetylacetonato was added, and then the Schlenk flask was sufficiently dried under a reduced pressure, followed by being filled with a dried argon. Under an atmosphere of the dried argon, 40.0 mL of nitrobenzene and 0.0375 mL (0.424 mmol) of trifluoromethanesulfonic acid were added, and then agitated at 25° C. for 3 hours to measure an absorption spectrum. A wavelength of the absorption maximum belonging in the absorption band located at the longest wavelength side was 573 nm, and Ai=0.24052 was determined.

In the above solution, 0.003 mL (0.17 mmol) of water was added, and then agitated at 25° C. for 1 hour; further adding 0.003 mL (0.17 mmol) of water in the above solution, and then agitating at 25° C. for 1 hour; and then still further adding 0.003 mL (0.17 mmol) of water in the above solution, and then agitating at 25° C. for 1 hour to measure an absorption spectrum. According to the absorbance at the wavelength of 573 nm, Af=0.13921 was determined. According to the above results, the parameter P of the catalyst was determined as 0.58.

Determination of Parameter Eo:

In a measuring flask having a capacity of 50 mL, 1.96 g (5 mmol) of tetra-n-butylammoniumtrifluoromethanesulfonate and 40 mL of nitrobenzene were put in, degassed by bubbling for 30 minutes with the dried argon, added with 111 μL (1.25 mmol) of trifluoromethanesulfonic acid and 0.71 mL (5 mmol) of anhydrous trifluoroacetic acid, and then messed up with nitrobenzene to prepare a supporting electrolyte solution.

In 10 mL of this supporting electrolyte solution, under an atmosphere of a dried nitrogen, 26.5 mg (0.10 mmol) of vanadyl acetylacetonato was added, maintained at 25° C. for 6 hours, and then subjected to the cyclic voltammetry measurement. This measurement resulted in Epa=1.15 (V Fc/Fc+standard) and Epc=0.95 (V Fc/Fc+standard). According to the above results, the parameter Eo of the catalyst was determined as 1.05 (V).

In this cyclic voltammetry measurement, a redox pair was also observed at 1.23 (V Fc/Fc+standard).

Example 3

Polymerization of 1,4-dibutoxybenzene (Parameter P: 0.66, Parameter Eo: 0.78)

71.5 mg (0.084 mmol) of bis-μ-(3,3'-(5-t-butyl-1,3-phenylenebis(methylene))bis(2,4-pentanedionato))divanadium (IV)oxide was dissolved in 0.67 mL of nitrobenzene and 0.037 mL (0.42 mmol) of trifluoromethanesulfonic acid, and then agitated under an oxygen atmosphere at 25° C. for 1 hour. The solution obtained above was added with a solution composed of 500.1 mg (2.25 mmol) of 1,4-dibutoxybenzene and 1.48 mL of nitrobenzene, and then agitated under the oxygen atmosphere at 25° C. for 48 hours. Thereafter, the reaction solution was dropped into a hydrochloric acidic methanol, followed by subjecting the precipitation obtained to filtration, washing, and drying to obtain 63.42 mg of polymer (yield 12.8%). Mn=2300, Mw=4100.

Determination of Parameter P

In a Schlenk flask having 50 cc capacity, 72.0 mg (0.085 mmol) of bis-µ-(3,3'-(5-t-butyl-1,3-phenylenebis(methylene))bis(2,4-pentanedionato))divanadium(IV)oxide was added, and then the Schlenk flask was sufficiently dried under a reduced pressure, followed by being filled with a dried argon. Under an atmosphere of the dried argon, 40.0 mL of nitrobenzene and 0.038 mL (0.425 mmol) of trifluoromethanesulfonic acid were added, and then agitated at 25° C. for 3 hours to measure an absorption spectrum. A wavelength of the absorption maximum belonging in the absorption band located at the longest wavelength side was 614 nm, and Ai=1.43868 was determined. In the above solution, 0.003 mL (0.17 mmol) of water was added, and then agitated at 25° C. for 1 hour; further adding 0.003 mL (0.17 mmol) of water in the above solution, and then agitating at 25° C. for 1 hour; and then still further adding 0.003 mL (0.17 mmol) of water in the above solution, and then agitating at 25° C. for 1 hour to measure an absorption spectrum. According to the absorbance at the wavelength of 614 nm, Af=0.94769 was determined. According to the above results, the parameter P of the catalyst was determined as 0.66.

Determination of Parameter Eo:

In a measuring flask having a capacity of 50 mL, 1.96 g (5 mmol) of tetra-n-butylammoniumtrifluoromethanesulfonate and 40 mL of nitrobenzene were put in, degassed by bubbling for 30 minutes with the dried argon, added with 111 µL (1.25 mmol) of trifluoromethanesulfonic acid and 0.71 mL (5 mmol) of anhydrous trifluoroacetic acid, and then messed up with nitrobenzene to prepare a supporting electrolyte solution.

In 10 mL of this supporting electrolyte solution, under an atmosphere of a dried nitrogen, 42.34 mg (0.05 mmol) of bis-µ-(3,3'-(5-t-butyl-1,3-phenylenebis(methylene))bis(2,4-pentanedionato))divanadium(IV)oxide was added, maintained at 25° C. for 6 hours, and then subjected to the cyclic voltammetry measurement. This measurement resulted in Epa=0.94 (V Fc/Fc+standard) and Epc=0.62 (V Fc/Fc+standard). According to the above results, the parameter Eo of the catalyst was determined as 0.78 (V).

In this cyclic voltammetry measurement, a redox pair derived from a catalyst not activated at 0.47 (V Fc/Fc+standard) was observed, and a redox pair at 1.10 (V Fc/Fc+standard) was also observed.

Comparative Example 1

Polymerization of 1,4-dibutoxybenzene (Parameter P: 0.36, Parameter Eo: 0.56)

22.45 mg (0.088 mmol) of vanadyl acetylacetonato was dissolved in 0.34 mL of nitrobenzene and 0.007 mL (0.079 mmol) of trifluoromethanesulfonic acid, and then agitated under an oxygen atmosphere at 25° C. for 1 hour. The solution obtained above was added with a solution composed of 244.9 mg (1.13 mmol) of 1,4-dibutoxybenzene and 0.79 mL of nitrobenzene, and then agitated under an oxygen atmosphere at 25° C. for 55 hours. Thereafter, the reaction solution was dropped into a hydrochloric acidic methanol, followed by subjecting the precipitation obtained to filtration, washing, and drying to obtain 0.7 mg of polymer (yield 0.3%). Measuring average molecular numbers thereof was impossible.

Determination of Parameter P

In a Schlenk flask having 50 cc capacity, 44.55 mg (0.168 mmol) of vanadyl acetylacetonato was added, and then the Schlenk flask was sufficiently dried under a reduced pressure, followed by being filled with a dried argon. Under an atmosphere of the dried argon, 40.0 mL of nitrobenzene and 0.015 mL (0.170 mmol) of trifluoromethanesulfonic acid were added, and then agitated at 25° C. for 3 hours to measure an absorption spectrum. A wavelength of the absorption maximum belonging in the absorption band located at the longest wavelength side was 573 nm, and Ai=0.31835 was determined. In the above solution, 0.003 mL (0.17 mmol) of water was added, and then agitated at 25° C. for 1 hour; further adding 0.003 mL (0.17 mmol) of water in the above solution, and then agitating at 25° C. for 1 hour; and then still further adding 0.003 mL (0.17 mmol) of water in the above solution, and then agitating at 25° C. for 1 hour to measure an absorption spectrum. According to the absorbance at the wavelength of 573 nm, Af=0.11514 was determined. According to the above results, the parameter P of the catalyst was determined as 0.36.

Determination of Parameter Eo:

In a measuring flask having a capacity of 50 mL, 1.96 g (5 mmol) of tetra-n-butylammoniumtrifluoromethanesulfonate and 40 mL of nitrobenzene were put in, degassed by bubbling for 30 minutes with the dried argon, added with 44 µL (0.50 mmol) of trifluoromethanesulfonic acid and 0.71 mL (5 mmol) of anhydrous trifluoroacetic acid, and then messed up with nitrobenzene to prepare a supporting electrolyte solution. In 10 mL of this supporting electrolyte solution, under an atmosphere of a dried nitrogen, 26.5 mg (0.10 mmol) of vanadyl acetylacetonato was added, maintained at 25° C. for 6 hours, and then subjected to the cyclic voltammetry measurement. This measurement resulted in Epa=0.62 (V Fc/Fc+standard) and Epc=0.50 (V Fc/Fc+standard). According to the above results, the parameter Eo of the catalyst was determined as 0.56 (V).

In this cyclic voltammetry measurement, a redox pair at 0.77 (V Fc/Fc+standard) was also observed.

Comparative Example 2

Polymerization of 1,4-dibutoxybenzene (Parameter P: 0.58, Parameter Eo: 0.40)

112.93 mg (0.33 mmol) of (N,N'-ethylenebis(salicylideneaminate))oxovanadium(IV) was dissolved in 1.35 mL of nitrobenzene and 0.075 mL (0.084 mmol) of trifluoromethanesulfonic acid, and then agitated under an oxygen atmosphere at 25° C. for 1 hour. The solution obtained above was added with a solution composed of 1.00 g (4.5 mmol) of 1,4-dibutoxybenzene and 6.0 mL of nitrobenzene, and then agitated under an oxygen atmosphere at 40° C. for 48 hours. Thereafter, the reaction solution was dropped into methanol, followed by subjecting the precipitation obtained to filtration, washing, and drying to obtain 11.4 mg of polymer (yield 1.1%). Mn=1800, Mw=2300.

Determination of Parameter P

In a Schlenk flask having 50 cc capacity, 56.7 mg (0.17 mmol) of (N,N'-ethylenebis(salicylideneaminate))oxovanadium(IV) was added, and then the Schlenk flask was sufficiently dried under a reduced pressure, followed by being filled with a dried argon. Under an atmosphere of the dried argon, 40.0 mL of nitrobenzene and 0.038 mL (0.425 mmol) of trifluoromethanesulfonic acid were added, and then agitated at 25° C. for 3 hours to measure an absorption spectrum. A wavelength of the absorption maximum belonging in the absorption band located at the longest wavelength side was 617 nm, and Ai=0.44624 was determined. In the above solution, 0.003 mL (0.17 mmol) of water was added, and then agitated at 25° C. for 1 hour; further adding 0.003 mL (0.17 mmol) of water in the above solution, and then agitating at 25° C. for 1 hour; and then still further adding 0.003 mL (0.17 mmol) of water in the above solution, and then agitating at 25° C. for 1 hour to measure an absorption spectrum. According to the absorbance at the wavelength of 617 nm, Af=0.23412 was determined. According to the above results, the parameter P of the catalyst was determined as 0.52.

Determination of Parameter Eo:

In a measuring flask having a capacity of 50 mL, 1.96 g (5 mmol) of tetra-n-butylammoniumtrifluoromethanesulfonate and 40 mL of nitrobenzene were put in, degassed by bubbling for 30 minutes with the dried argon, added with 111 μL (1.25 mmol) of trifluoromethanesulfonic acid and 0.71 mL (5 mmol) of anhydrous trifluoroacetic acid, and then messed up with nitrobenzene to prepare a supporting electrolyte solution. In 10 mL of this supporting electrolyte solution, under an atmosphere of a dried nitrogen, 33.3 mg (0.10 mmol) of (N,N'-ethylenebis(salicylideneaminate))oxovanadium(IV) was added, maintained at 25° C. for 6 hours, and then subjected to the cyclic voltammetry measurement. This measurement resulted in Epa=0.49 (V Fc/Fc+standard) and Epc=0.31 (V Fc/Fc+standard). According to the above results, the parameter Eo of the catalyst was determined as 0.40 (V).

In this cyclic voltammetry measurement, a redox pair at 0.07 (V Fc/Fc+standard) was also observed.

Example 4

Parameter P: 0.93, Parameter Eo: 0.90, the Catalyst being Same as in Example 1

Polymerization of 2,8-dioctyloxydibenzofuran

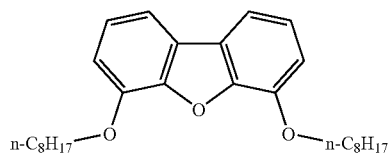

(2,8-dioctyloxydibenzofuran) Oxidation side peak potential 1.03 (V Fc/Fc+standard)

32.40 mg (0.044 mmol) of bis-μ-(3,3'-(1,3-phenylenebis (methylene))bis(2,4-pentanedionato))divanadium(IV)oxide was dissolved in 0.35 mL of nitrobenzene and 0.020 mL (0.23 mmol) of trifluoromethanesulfonic acid, and then agitated under an oxygen atmosphere at 25° C. for 1 hour. The solution obtained above was added with a solution composed of 500.6 mg (1.18 mmol) of 2,8-dioctyloxydibenzofuran and 1.48 mL of nitrobenzene, and then agitated under an oxygen atmosphere at 25° C. for 100 hours. When a water content was measured after elapsing 1 hour from the commencement of the agitation, the water content in the reaction solution was 0.74 mg (0.04 mmol) and 0.5 equivalent of water per mole of the metal contained in the catalyst was detected. Thereafter, the reaction solution was dropped into a hydrochloric acidic methanol, followed by subjecting the oily substance obtained to separation and drying to obtain 53.45 mg of polymer (yield 10.7%). Mn=2200, Mw=3700.

Example 5

Synthesis of bis-μ-(3,3'-(1,3-phenylenebis(methylene))bis(2,4-pentanedionato))divanadium(IV)oxide (The minimum number of the bondings interposing between the coordinating atoms was 10)

Ligand

Synthesis of 3,3'-[1,3-phenylenebis(methylene)]bis (2,4-pentanedione)

17.0 g (0.15 mol) of t-butokypotassium was added to 20 mL of t-butylalcohol, and then dissolved by agitating for 30 minutes under refluxing. In the above solution, under refluxing, 22.9 g (0.23 mol) of acetylacetone was dropped for 10 minutes, and then agitated for 2 hours. Thereafter, under refluxing, 20.2 g (0.08 mol) of 1,3-bis(bromomethyl)benzene was added for 30 minutes, and then agitated for 1 hour. Thereafter, under refluxing, 3.0 g (0.02 mol) of potassium iodide was added, and then agitated for 4 hours. After the completion of the agitation, the solution was cooled down to a room temperature, added with 100 mL of water, and 100 mL of diethylether, strongly agitated, and then an organic layer was separated from a water layer. The organic layer was washed twice with 100 mL of saturated aqueous salt solution, and then the organic layer was dried with anhydrous sodium sulfate, concentrated by removing the solvent and excess amount of acetylacetone under a reduced pressure to obtain a light-yellow oily crude product. The crude product was purified with a silica gel column chromatography to obtain a white solid (yield in amount 3.5 g, yield in ratio 15.1%)

$^1$H-NMR (chloroform-d, ppm): 2.07 (s, 12H), 4.42 (s, 4H), 6.95 to 7.00 (m, 3H), 7.22 to 7.27 (m, 1H), 16.80 (s, 1H)

$^{13}$C-NMR (chloroform-d, ppm): 23.6, 33.1, 108.5, 125.6, 127.1, 129.4, 140.5, 192.1

Synthesis of bis-μ-(3,3'-(1,3-phenylenebis(methylene))bis(2,4-pentanedionato))divanadium(IV)oxide In a solution composed of 102.4 mg (0.34 mmol) of the above-synthesized 3,3'-[1,3-phenylenebis(methylene)]bis(2,4-pentanedione) and 3.8 mL of ethanol, a solution composed of 74.7 mg (0.34 mmol) of vanadyl sulfate trihydrate and 3.3 mL of 50% aqueous ethanol solution was dropped at 25° C. for 10 minutes. After agitating at 25° C. for 4 hours, a precipitated solid was collected with a filtration, washed with 50% aqueous ethanol solution, and diethylether, and then dried at 40° C. under a reduced pressure to obtain the intended complex as a light green powder (yield in amount 41.3 g, yield in ratio 33%).

Elemental analysis/calculated value: C (58.9%), H (5.5%), O (21.8%)/measured value: C (58.7%), H (5.7%), O (21.1%)
FD-MS: m/z 734, 367

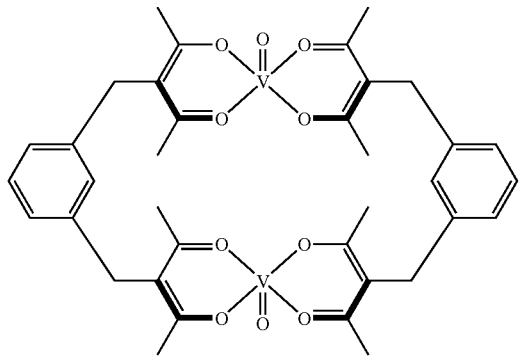

bis-μ-(3,3'-(1,3-phenylenebis(methylene))bis(2,4-pentanedionato))divanadium(IV)oxide Example 6

Synthesis of bis-μ-(3,3'-(5-t-butyl-1,3-phenylenebis(methylene))bis(2,4-pentanedionato))divanadium(IV)oxide (The minimum number of the bondings interposing between the coordinating atoms was 10)

Ligand

Synthesis of 3,3'-[5-t-butyl-1,3-phenylenebis(methylene)]bis(2,4-pentanedione)

In a four-neck flask having a capacity of 500 mL, 19.6 g (175 mmol) of t-butokypotassium and 300 mL of t-butylalcohol were put in, agitated at a temperature of 82° C. for 30 minutes, dropped with 26.5 g (262 mmol) of acetylacetone at the temperature for 12 minutes, and then agitated for 2 hours. Thereafter, at 81 to 83° C., 25.0 g (87.3 mmol) of 1,3-bis(bromomethyl)-5-t-butylbenzene was added for 30 minutes, and then agitated for 1 hour. Thereafter, 3.49 g (21.0 mmol) of potassium iodide was added at 82° C., and then agitated for 3.5 hours. After the solution was cooled down to a room temperature, it was added with 100 mL of diethylether, and 115 mL of water to be subjected to an extraction operation, and then an organic layer was separated from a water layer. The organic layer obtained was added with 30 mL of saturated aqueous salt solution and agitated, and then an organic layer was separated from a water layer, dried with anhydrous sodium sulfate, and then concentrated by distilling off the solvent to obtain a crude product. The crude product obtained was purified with a silica gel column chromatography to obtain 21.9 g (yield 69%) of 3,3'-[5-t-butyl-1,3-phenylenebis(methylene)]bis(2,4-pentanedione)
GC-MS m/z: 358 (M+), 340, 315, 240, 215, 197

Synthesis of bis-μ-(3,3'-(5-t-butyl-1,3-phenylenebis(methylene))bis(2,4-pentanedionato))divanadium(IV)oxide In a solution composed of 2.71 g (7.56 mmol) of the above-synthesized 3,3'-[5-t-butyl-1,3-phenylenebis(methylene)]bis(2,4-pentanedione), 1.52 g (15.0 mmol) of triethylamine, and 538 mL of N,N-dimethylformamide, a solution composed of 1.71 g (7.56 mmol) of vanadyl sulfate trihydrate and 538 mL of N,N-dimethylformamide was dropped at 25° C. for 1 hour. After agitating at 20 to 25° C. for 48 hours, a precipitated solid was collected with a filtration, washed with N,N-dimethylformamide, and diethylether, and then dried at 70° C. under a reduced pressure to obtain the intended complex as a green powder (yield in amount 2.55 g, yield in ratio 80%)
Elemental analysis Calculated value: C (62.4%), H (6.7%), O (18.9%)
Measured value: C (62.7%), H (6.7%), O (18.1%)
FD-MS: m/z 846, 423

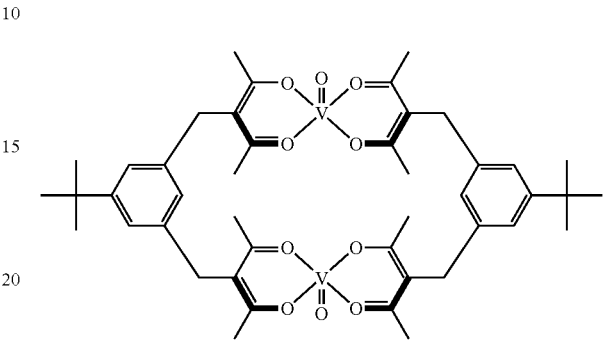

bis-μ-(3,3'-(5-t-butyl-1,3-phenylenebis(methylene))bis(2,4-pentanedionato))divanadium(IV)oxide Example 7

Synthesis of bis-μ-(3,3'-(2,4,5,6-tetrafluoro-1,3-phenylenebis(methylene))bis(2,4-pentanedionato))divanadium(IV)oxide (The minimum number of the bondings interposing between the coordinating atoms was 10)

Ligand

Synthesis of 3,3'-[2,4,5,6-tetrafluoro-1,3-phenylenebis(methylene)]bis(2,4-pentanedione)

In a four-neck flask, 6.66 g (59.4 mmol) of t-butokypotassium and 128 mL of t-butylalcohol were put in, agitated at a temperature of 82° C. for 30 minutes, dropped with 9.01 g (89.1 mmol) of acetylacetone for 12 minutes at the temperature, and then agitated for 2 hours. Thereafter, at 83° C., 12.8 g (purity 78.0%, 29.7 mmol) of 1,3-bis(bromomethyl)-2,4,5,6-tetrafluorobenzene was added for 25 minutes, and then agitated for 1 hour. Thereafter, 1.18 g (7.13 mmol) of potassium iodide was added at 82° C., and then agitated for 2 hours. After the solution was cooled down to a room temperature, it was added with 200 mL of diethylether, and 300 mL of water to be subjected to an extraction operation, and then an organic layer was separated from a water layer. The organic layer obtained was added with 300 mL of saturated aqueous salt solution and agitated, and then an organic layer was separated from a water layer, dried with anhydrous sodium sulfate, concentrated by distilling off the solvent, and then purified with silica gel column chromatography to obtain 7.2 g of a crude product. 4.66 g of the crude product obtained was re-crystallized with a mixed solvent of hexane and ethylacetate to obtain 1.46 g (yield 20%) of 3,3'-[2,4,5,6-tetrafluoro-1,3-phenylenebis(methylene)]bis(2,4-pentanedione)
GC-MS m/z: 374(M+), 331, 289, 269, 231, 189

Synthesis of bis-μ-(3,3'-(2,4,5,6-tetrafluoro-1,3-phenylenebis(methylene))bis(2,4-pentanedionato))divanadium(IV)oxide A solution composed of 82.7 mg (0.22 mmol) of 3,3'-[2,4,5,6-tetrafluoro-1,3-phenylenebis(methylene)]bis(2,4-pentanedione) and 2 mL of N,N-dimethylformamide was agitated in advance; the solution was added at a room temperature with a solution composed of 50.2 mg (0.22 mmol) of vanadyl sulfate trihydrate, 2 mL of N,N-dimethylformamide, and 3 mL of water, adjusted to pH 5.0 with sodium carbonate solution, and then agitated at a room temperature for 4.5 hours. A precipitated crystal was collected with a filtration, washed, and then dried under a reduced pressure to obtain 19.3 mg (yield 20%) of bis-μ-(3,3'-(2,4,5,6-tetrafluoro-1,3-phenylenebis(methylene))bis(2,4-pentanedionato))divanadium(IV)oxide.

Elemental analysis Calculated value: C (49.2%), H (3.7%)
Measured value: C (50.8%), H (4.1%)
FD-MS: m/z 878, 813, 439, 374

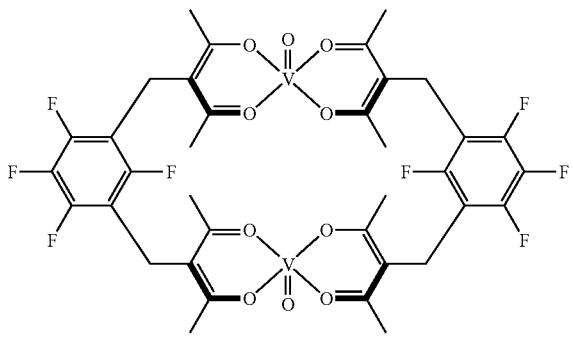

bis-μ-(3,3'-(2,4,5,6-tetrafluoro-1,3-phenylenebis(methylene))bis(2,4-pentanedionato))divanadium(IV)oxide

INDUSTRIAL APPLICABILITY

According to the invention, in an oxidative polymerization of an aromatic compound, an aromatic compound polymer can be obtained in a relatively favorable yield without using large amount of a dehydrating agent.

The invention claimed is:

1. A method for producing an aromatic compound polymer by oxidatively polymerizing one or more of aromatic compound(s) having two or more hydrogen atoms directly connected to aromatic ring(s), in the presence of an oxidizing agent, wherein the method employs a catalyst composed of a transition metal complex or a catalyst prepared from a transition metal complex and an activating agent, and said catalyst has a parameter P defined by the following formula (A) of 0.50 or more, and a parameter Eo defined by the following formula (B) of 0.50 [V] or more:

$$P = Af/Ai \quad (A)$$

(wherein Ai represents an absorbance at an absorption maximum belonging in an absorption band located at the longest wavelength side in an absorption spectrum obtained for a solution containing the catalyst, in a ultraviolet to near-infrared wavelength region from 200 nm to 800 nm, and Af represents an absorbance at the same wavelength applied to the Ai, in an absorption spectrum in the above wavelength region obtained for a solution prepared by adding 3 equivalent of water per mole of the metal contained in the catalyst to the solution), and $$Eo = (Epa + Epc)/2 \ [V] \quad (B)$$

(wherein, Epa represents a peak potential at the oxidation side of an oxidation-reduction potential derived from the transition metal contained in the catalyst at a potential of 0.50 [V] or more based on oxidation-reduction potential of ferrocene/ferrocenium ion measured with a cyclic voltammetry for the solution containing the catalyst, and Epc represents a peak potential at the reduction side corresponding to Epa by the same measurement);

wherein the aromatic compound polymer is a polymer of the aromatic compound(s) in which two or more hydrogen atoms having been directly connected to aromatic ring(s) are removed.

2. The method according to claim 1, wherein the oxidizing agent is oxygen.

3. The method according to claim 1, wherein the transition metal complex is a vanadium complex.

4. The method according to claim 1, wherein the catalyst is a catalyst prepared from a vanadium complex and an acid.

5. The method according to claim 3, wherein the vanadium complex is a vanadium di-nuclear complex.

6. The method according to claim 5, wherein the vanadium di-nuclear complex is a vanadium di-nuclear complex represented by the general formula (1):

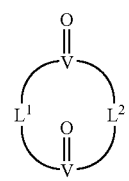

(1)

(wherein $L^1$ and $L^2$ respectively represent a ligand having 4 or more coordinating atoms and respectively connect to two vanadium atoms by the coordinating atom respectively).

7. The method according to claim 3, wherein the vanadium complex is a vanadium mononuclear complex.

8. The method according to claim 7, wherein an amount of the acid is more than 2 mole times per mole of the vanadium mononuclear complex.

9. The method according to claim 1, wherein an amount of water present in a reaction mixture at the completion of the oxidative polymerization reaction is 0.01 moles or more per 1 mole of the metal contained in the catalyst.

10. An aromatic compound polymer produced by the method according to claim 1.

11. The method according to claim 1, wherein
the aromatic compound(s) having two or more hydrogen atoms directly connected to aromatic ring(s) is represented by formula (2), and
the aromatic compound polymer contains a repeating unit represented by formula (3):

(2)

wherein $Ar^1$ and $Ar^2$ each independently represent arylene group or divalent aromatic heterocyclic group; X represents a single bond or divalent bonding structure; and n represents an integer of zero or more; and when X and $Ar^2$ exist in a plural number respectively, they may respectively be same as or different from each other;

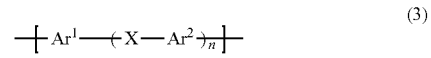

(3)

wherein $Ar^1$, $Ar^2$, X and n respectively represent the same meaning as mentioned above.

* * * * *